US006809102B2

(12) United States Patent
Kimball et al.

(10) Patent No.: US 6,809,102 B2
(45) Date of Patent: Oct. 26, 2004

(54) CYANO-SUBSTITUTED DIHYDROPYRIMIDINE COMPOUNDS AND THEIR USE TO TREAT DISEASES

(75) Inventors: Spencer David Kimball, East Windsor, NJ (US); Louis J. Lombardo, Belle Mead, NJ (US); David B. Rawlins, Morrisville, PA (US); Hai-Yun Xiao, Princeton, NJ (US); Robert J. Schmidt, Hainesport, NJ (US); David K. Williams, Delran, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/104,257

(22) Filed: Mar. 22, 2002

(65) Prior Publication Data
US 2003/0008888 A1 Jan. 9, 2003

Related U.S. Application Data
(60) Provisional application No. 60/279,956, filed on Mar. 29, 2001.

(51) Int. Cl.[7] .................... A61K 31/513; A61K 31/505; C07D 239/22
(52) U.S. Cl. ........................ 514/256; 514/274; 544/316; 544/323; 544/324
(58) Field of Search ................ 544/316, 323, 544/324; 514/256, 274

(56) References Cited

U.S. PATENT DOCUMENTS

| | | | | |
|---|---|---|---|---|
| 5,942,517 | A | 8/1999 | Nagarathnam et al. | 514/274 |
| 6,080,760 | A | 6/2000 | Patane et al. | 514/326 |
| 6,172,066 | B1 | 1/2001 | Nagarathnam et al. | 514/252 |
| 6,211,198 | B1 | 4/2001 | Gluchowski et al. | 514/318 |
| 6,284,480 | B1 | 9/2001 | Nislow et al. | 435/21 |
| 2002/0143026 | A1 | 10/2002 | Lombardo et al. | 514/269 |

FOREIGN PATENT DOCUMENTS

| | | | |
|---|---|---|---|
| JP | 42002265 | * | 2/1967 |
| WO | WO 96/14846 | | 5/1996 |
| WO | WO 97/17969 | | 5/1997 |
| WO | WO 97/42956 | | 11/1997 |
| WO | WO 98/57639 | | 12/1998 |
| WO | WO 99/25345 | | 5/1999 |
| WO | WO 99/50440 | | 10/1999 |
| WO | WO 00/20451 | | 4/2000 |
| WO | WO 01/05410 | | 1/2001 |
| WO | WO 01/07602 | | 2/2001 |
| WO | WO 01/30768 | | 5/2001 |
| WO | WO 01/31335 | | 5/2001 |

OTHER PUBLICATIONS

Takamizawa et al., Chemical Abstracts, vol. 66:95074 (1967).*
Kuno A. et al., Chem. Pharm. Bull. 40(9): 2423–2431 (1992).
Prajapati D. and J.S. Sandhu, Chemistry Letters 10: 1945–1946, (1992).
Mayer et al., Science 286: 971–974 (1999).
Kaiser et al, J. Biol. Chem. 274(27): 18925–18931 (1999).
Barrow et al., J. Med. Chem. 43:2703–2718 (2000).
Hansen et al., Oncogene 18:6531–6539 (1999).
Blangy et al., Cell 83:1159–1169 (1995).
Sawin et al., Proc. Natl. Acad. Sci. USA 92:4289–4293 (1995).
Walczak et al., Cell 85: 943–946 (1996).
Gagliio et al., J. Cell Biol. 135(2): 399–414 (1996).
Whitehead et al., J. Cell Sci. 111: 2551–61 (1998).
Turner et al., J. Biol. Chem. 276(27): 25496–25502 (2001).

* cited by examiner

Primary Examiner—Richard L. Raymond
(74) Attorney, Agent, or Firm—Maureen S. Gibbons

(57) ABSTRACT

The present invention provides compounds of formula I

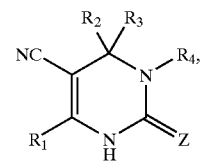

and pharmaceutically acceptable salts thereof.

The formula I compounds induce mitotic arrest thereby making them useful as anti-cancer agents. The formula I compounds are also useful for the treatment of other diseases which can be treated by inducing mitotic arrest.

32 Claims, No Drawings

CYANO-SUBSTITUTED DIHYDROPYRIMIDINE COMPOUNDS AND THEIR USE TO TREAT DISEASES

RELATED APPLICATIONS

This application claims the benefit under 35 U.S.C. Section 119(e) of U.S. Provisional Patent Application No. 60/279,956 filed Mar. 29, 2001.

FIELD OF INVENTION

This invention relates to novel compounds that interrupt mitosis thereby making the compounds useful for the treatment of proliferative diseases, such as cancer.

BACKGROUND

Cell proliferation and programmed cell death play important roles in the growth and development of an organism. In proliferative diseases such as cancer, the processes of cell proliferation and/or programmed cell death are often perturbed. For example, a cancer cell may have unregulated cell division through either the overexpression of a positive regulator of the cell cycle or the loss of a negative regulator of the cell cycle, perhaps by mutation. Alternatively, a cancer cell may have lost the ability to undergo programmed cell death through the overexpression of a negative regulator of apoptosis. Hence, there is a need to develop new chemotherapeutic drugs that will restore the processes of checkpoint control and programmed cell death to cancerous cells.

One approach to the treatment of human cancers is to target a protein that is essential for cell cycle progression. In order for the cell cycle to proceed from one phase to the next, certain prerequisite events must be completed. There are checkpoints within the cell cycle that enforce the proper order of events and phases. One such checkpoint is the spindle checkpoint that occurs during the metaphase stage of mitosis. Small molecules that target proteins with essential functions in mitosis may initiate the spindle checkpoint to arrest cells in mitosis. Of the small molecules that arrest cells in mitosis, those which display anti-tumor activity in the clinic also induce apoptosis, the morphological changes associated with programmed cell death. An effective chemotherapeutic for the treatment of cancer may be one that induces checkpoint control and subsequent programmed cell death.

Most compounds known to cause mitotic arrest and apoptosis act as tubulin binding agents. These compounds alter the dynamic instability of microtubules and indirectly alter the function/structure of the mitotic spindle thereby causing mitotic arrest. Because most of these compounds target the tubulin protein, a component of all microtubules, they may also affect normal cellular processes in which microtubules have a role. Hence, a need exists for small molecules that specifically target proteins associated with proliferating cells, such as Eg5.

Eg5 is one of several kinesin-like motor proteins that are localized to the mitotic spindle and known to be required for formation and/or function of the bipolar mitotic spindle. Recently, there was a report of a small molecule that disturbs bipolarity of the mitotic spindle (Mayer, T. U. et. al. 1999. Science 286(5441) 971–4).

More specifically, the small molecule induced the formation of an aberrant mitotic spindle wherein a monoastral array of microtubules emanated from a central pair of centrosomes, with chromosomes attached to the distal ends of the microtubules. The small molecule was dubbed "monastrol" after the monoastral array. This monoastral array phenotype had been previously observed in mitotic cells that were immunodepleted of the Eg5 motor protein.

The distinctive monoastral array phenotype facilitated identification of monastrol as a potential inhibitor of Eg5. Indeed, monastrol was further shown to inhibit the Eg5 motor-driven motility of microtubules in an in vitro assay. Furthermore, monastrol had no apparent effect upon the related kinesin motor or upon the motor(s) responsible for golgi apparatus movement within the cell. Cells that display the monoastral array phenotype, either through immunodepletion of Eg5 or monastrol inhibition of Eg5, arrest in M-phase of the cell cycle. Unfortunately, however, the mitotic arrest induced by either of these mechanisms is transient. (Kapoor, 2000. *J. Cell. Biol.* 150(5) 975–80). Both the monoastral array phenotype and the monastrol induced cell cycle arrest in mitosis are reversible. Cells recover to form a normal bipolar mitotic spindle, to complete mitosis, and to proceed through the cell cycle and normal cell proliferation. This suggests that a small molecule inhibitor of Eg5 that induced a transient mitotic arrest may not be effective for the treatment of cancer cell proliferation. Nonetheless, the discovery that monastrol causes mitotic arrest is intriguing and hence there is a need to further study and identify compounds that can be used to modulate the Eg5 motor protein in a manner that would be effective in the treatment of human cancers. There is also a need to explore the use of these compounds in combination with other antineoplastic agents.

SUMMARY

The compounds of the invention cause the interruption of mitosis, and as such, can be used to treat proliferative diseases. For example, the compounds of the instant invention can be used as antiproliferatives and anticancer agents. More specifically, the invention comprises a compound of formula I

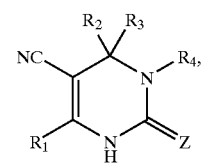

its enantiomers, diastereomers, pharmaceutically acceptable salts, prodrugs and solvates thereof, wherein $R_1$ is selected from the group consisting of hydrogen, alkyl and cycloalkyl;

$R_2$ and $R_3$ are each independently selected from the group consisting of H, alkyl, aryl, heteroaryl, arylalkyl, cycloalkyl, heterocycloalkyl, cycloalkylalkyl, heterocycloalkylalkyl and heteroarylalkyl; or $R_2$ and $R_3$ may also be taken together to form a carbocyclic or heterocyclic ring;

$R_4$ is selected from the group consisting of alkyl, arylalkyl, cycloalkylalkyl, heteroarylalkyl, heterocycloalkyl, aminoalkyl, heterocycloalkylalkyl, CN, $C(O)R_5$, $CO_2R_5$, $C(O)SR_5$ and $CONR_5R_6$;

$R_5$ and $R_6$ are each independently selected from the group consisting of H, alkyl, cycloalkyl, hydroxyalkyl, alkenyl, alkoxy, thioalkoxy, alkoxyalkyl, haloalkyl, aryl, heteroaryl, arylalkyl, cycloalkylalkyl, heteroarylalkyl and heterocycloalkylalkyl or N—$R_5R_6$ together form a heterocycloalkyl Z is selected from the group consisting of O, S and $NR_8$;

$R_8$ is selected from the group consisting of H, CN, sulfonamido, $OR_7$, alkyl, cycloalkyl, aryl, arylalkyl, heterocyclyl, heteroaryl and heteroarylalkyl; and $R_7$ is selected from the group consisting of H, alkyl, arylalkyl, cycloalkylalkyl, heterocycloalkylalkyl and heteroarylalkyl.

In a preferred embodiment, $R_2$ is a heteroaryl, such as an optionally substituted thiophene, oxazole, isoxazole, or furan. Preferred substituents include methyl, ethyl, halo, haloalkyl, or aryl groups.

According to one embodiment, $R_3$ is H and $R_2$ is an optionally substituted phenyl wherein the substituents are selected from the group consisting of alkyl, alkoxy, alkoxyalkyl, cyano, halo, haloalkyl, nitro, amino $CO_2R_5$, $CONR_5R_6$, alkenyloxy, aryloxy, wherein $R_5$ and $R_6$ are, independently, H or alkyl. Preferred substituents include methyl, methoxy, F, Cl, $CF_3$, dimethylamino, and ethoxymethyl, for example.

According to one embodiment of the present invention, $R_1$ is alkyl; $R_2$ is selected from the group consisting of aryl and heteroaryl; $R_3$ is H; $R_4$ is selected from the group consisting of alkyl, arylalkyl, $CO_2R_5$, and $CONR_5R_6$; $R_5$ and $R_6$ are independently selected from the group consisting of H, alkyl, aminoalkyl, hydroxyalkyl, phenylamino and arylalkyl; Z is selected from the group consisting of O, S, and $NR_8$; $R_8$ is selected from the group consisting of H and CN.

In a preferred embodiment, $R_4$ is selected from the group consisting of alkyl, arylalkyl, $C(O)R_5$ $CO_2R_5$, $C(O)SR_5$ and $CONR_5R_6$.

According to one embodiment, $R_4$ is $CO_2R_5$; Z is O; and $R_5$ is ethyl.

In another embodiment, $R_4$ is $CONR_5R_6$; Z is O; $R_5$ is H and $R_6$ is methyl, ethyl, propyl, phenyl, cyclopropyl, hydroxyethyl, thiophene, or 2-propylene.

In one embodiment of the present invention, $R_4$ is selected from the group consisting of alkyl and arylalkyl, and Z is O. In another embodiment $R_1$ is $CH_3$; $R_2$ is aryl; $R_4$ is $CO_2R_5$; $R_5$ is alkyl; and Z is O. In still another embodiment $R_1$ is $CH_3$; $R_2$ is aryl; $R_4$ is $CONR_5R_6$; $R_5$ is alkyl; $R_6$ is H and Z is O. In yet another embodiment, $R_1$ is $CH_3$; $R_2$ is heteroaryl; $R_4$ is $CO_2R_5$ or $CONR_5R_6$; $R_6$ is H and $R_5$ is ethyl.

The present invention also provides methods for preparing intermediates and compounds having Formula I.

The present invention also provides methods for treating a proliferative disease, such as cancer, via modulation of the Eg5 motor protein comprising administering to a mammalian species in need of such treatment an effective amount of at least one compound of formula I, as defined above.

DESCRIPTION

The present invention provides for compounds of formula I, as defined above, pharmaceutical compositions employing such compounds and methods of using such compounds.

Listed below are definitions of various terms used to describe the compounds of the instant invention. These definitions apply to the terms as they are used throughout the specification (unless they are otherwise limited in specific instances) either individually or as part of a larger group.

The term "alkyl" herein alone or as part of another group refers to a monovalent alkane (hydrocarbon) derived radical containing from 1 to 12 carbon atoms unless otherwise defined. An alkyl group is an optionally substituted straight, branched or cyclic saturated hydrocarbon group. When substituted, alkyl groups may be substituted with up to four substituent groups, R as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: aryl, halo (such as F, Cl, Br, I), haloalkyl (such as $CCl_3$ or $CF_3$), alkoxy, atkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH). Alkyl groups as defined may also comprise one or more carbon to carbon double bonds or one or more carbon to carbon triple bonds.

The term "alkenyl" herein alone or as part of another group refers to a hydrocarbon radical straight, branched or cyclic containing from 2 to 12 carbon atoms and at least one carbon to carbon double bond.

The term "alkynyl" herein alone or as part of another group refers to a hydrocarbon radical straight, branched or cyclic containing from 2 to 12 carbon atoms and at least one carbon to carbon triple bond.

The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms; examples include ethynyl, propynyl, butynyl, and hexynyl.

The term "cycloalkyl" herein alone or as part of another group is a specie of alkyl containing from 3 to 15 carbon atoms, without alternating or resonating double bonds between carbon atoms. It may contain from 1 to 4 rings. Exemplary unsubstituted such groups include cyclopropyl, cyclobutyl, cyclopentyl, cyclohexyl, adamantyl, etc. Exemplary substituents include one or more of the following groups: halogen, alkyl, alkoxy, alkyl hydroxy, amino, nitro, cyano, thiol and/or alkylthio.

The terms "alkoxy" or "alkylthio" herein alone or as part of another group denote an alkyl group as described above bonded through an oxygen linkage (—O—) or a sulfur linkage (—S—), respectively.

The term "alkyloxycarbonyl" herein alone or as part of another group denotes an alkoxy group bonded through a carbonyl group. An alkoxycarbonyl radical is represented by the formula: —C(O)OR, where the R group is a straight or branched $C_{1-6}$ alkyl group.

The term "alkylcarbonyl" herein alone or as part of another group refers to an alkyl group bonded through a carbonyl group.

The term "alkylcarbonyloxy" herein alone or as part of another group denotes an alkylcarbonyl group which is bonded through an oxygen linkage.

The term "arylalkyl" herein alone or as part of another group denotes an aromatic ring bonded to an alkyl group as described above.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkoxy, hydroxy, carboxy, carbamoyl, alkyloxycarbonyl, nitro, alkenyloxy, trifluoromethyl, amino, cycloalkyl, cyano, alkyl $S(O)_m$ (m=0, 1, 2), or thiol.

The term "amino" herein alone or as part of another group refers to —NH2. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl. carbonyl or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives The term "carbocyclic ring" herein alone or as part of another group refers to stable, saturated or partially unsaturated monocyclic ring hydrocarbyls of 3 to 7 carbon atoms such as cyclopropyl, cyclobutyl, cyclopentyl, cyclohexyl and cycloheptyl. The carbocyclic ring may be optionally substituted meaning that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino no), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower] alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "cycloalkyl" herein alone or as part of another group refers to fully saturated and partially unsaturated hydrocarbon rings of 3 to 9, preferably 3 to 7 carbon atoms. Further, a cycloalkyl may be substituted. A substituted cycloalkyl refers to such rings having one, two, or three substituents, preferably one, selected from the group consisting of halo, alkyl, substituted alkyl, alkenyl, alkynyl, nitro, cyano, oxo (=O), hydroxy, alkoxy, thioalkyl, —CO$_2$H, —C(=O)H, CO$_2$-alkyl, —C(=O)alkyl, keto, =N—OH, =N—O-alkyl, aryl, heteroaryl, heterocyclo, a five or six membered ketal (i.e. 1,3-dioxolane or 1,3-dioxane), —NR'R", —C(=O)NR'R", —CO$_2$NR'R", —C(=O)NR'R", —NR'CO$_2$'R", —NR'C(=O)R", —SO$_2$NR'R", and —NR'SO$_2$'R", wherein each of R' and R" is independently selected from hydrogen, alkyl, substituted alkyl, and cycloalkyl, or R' and R" together form a heterocyclo or heteroaryl ring.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, aryl, nitro, cyano, hydroxy, alkoxy, thioalkyl, —CO$_2$H, —C(=O)H, —CO$_2$-alkyl, —C(=O) alkyl, phenyl, benzyl, phenylethyl, phenyloxy, phenylthio, cycloalkyl, substituted cycloalkyl, heterocyclo, heteroaryl, —NR'R", —C(=O)NR'R", —CO$_2$NR'R", —C(=O) NR'R", —NR'CO$_2$'R", —NR'C(=O)R", —SO$_2$NR'R", and —NR'SO$_2$'R", wherein each of R' and R" is independently selected from hydrogen, alkyl, substituted alkyl, and cycloalkyl, or R' and R" together form a heterocyclo or heteroaryl ring.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "heterocycloalkyl" herein alone or as part of another group refers to a cycloalkyl group (nonaromatic) in which one of the carbon atoms in the ring is replaced by a heteroatom selected from O, S or N, and in which up to three additional carbon atoms may be replaced by said heteroatoms.

The term "heterocyclic ring" herein alone or as part of another group refers to a stable, saturated, or partially unsaturated monocyclic ring system containing 5 to 7 ring members of carbon atoms and other atoms selected from nitrogen, sulfur and/or oxygen. Preferably, a heterocyclyl is a 5 or 6-membered monocyclic ring and contains one, two, or three heteroatoms selected from nitrogen, oxygen and/or sulfur. The heterocyclic ring may be optionally substituted which means that the heterocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino),cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocyclic rings are isoxazolyl, imidazolinyl, thiazolinyl, imidazolidinyl, pyrrolyl, pyrrolinyl, pyranyl, pyrazinyl, piperidyl, morpholinyl and triazolyl. The heterocyclic ring may be attached to the parent structure through a carbon atom or through any heteroatom of the heterocyclyl that results in a stable structure.

The term "heterocyclyl" herein alone or as part of another group as used herein refers to a stable, saturated, or partially unsaturated, monocyclic, bridged monocyclic, bicyclic, and spiro ring system containing carbon atoms and other atoms selected from nitrogen, sulfur and/or oxygen. Preferably, a heterocyclyl is a 5 or 6-membered monocyclic ring or an 8–11 membered bicyclic ring which consists of carbon atoms and contains one, two, or three heteroatoms selected from nitrogen, oxygen and/or sulfur. The term "optionally substituted" as it refers to "heterocyclyl" herein indicates that the heterocyclyl group may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocyclyl groups are isoxazolyl, imidazolinyl, thiazolinyl, imidazolidinyl, pyrrolyl, pyrrolinyl, pyranyl, pyrazinyl, piperidyl, morpholinyl and triazolyl. The heterocyclyl group may be attached to the parent structure through a carbon atom or through any heteroatom of the heterocyclyl that results in a stable structure.

The term "heteroatom" means O, S or N, selected on an independent basis. It should be noted that any heteroatom with unsatisfied valences is assumed to have the hydrogen atom to satisfy the valences.

The term "halogen" or "halo" refers to chlorine, bromine, fluorine or iodine selected on an independent basis.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

As used herein, the term "patient" encompasses all mammalian species.

Suitable examples of salts of the compounds according to the invention with inorganic or organic acids are hydrochloride, hydrobromide, sulfate, methanesulfonate, maleate, fumarate, and phosphate. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form. The definition of the compounds according to the invention embraces all possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

It should be understood that the present invention includes prodrug forms of the compounds of formula I. Various forms of prodrugs are well known in the art. For examples of such prodrug derivatives, see:

(a) Design of Prodrugs, edited by H. Bundgaard (Elsevier, 1985); and Methods in Enzymology, Vol. 42, pp. 309–396, edited by K. Widder et al., (Academic Press, 1985);

(b) A Textbook of Drug Design and Development, edited by Krosgaard-Larsen and H. Bundgaard, Chapter 5, "Design and Application of Prodrugs," by H. Bundgaard, pp. 113–191 (1991);

(c) H. Bundgaard, Advanced Drug Deliver Reviews, 8, pp. 1–38 (1992);

(d) H. Bundgaard et al., Journal of Pharmaceutical Sciences, 77, 285 (1988); and (e) N. Kayeka et al., Chem. Phar. Bull., 32, 692 (1984).

In general, the instant invention comprises a compound of formula I

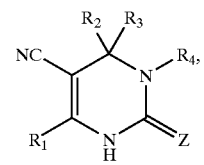

I its enantiomers, diastereomers, pharmaceutically acceptable salts, prodrugs and solvates thereof. $R_1$ is hydrogen, alkyl or cycloalkyl. $R_2$ and $R_3$ are each independently H, alkyl, aryl, heteroaryl, arylalkyl, cycloalkylalkyl, heterocycloalkylalkyl or heteroarylalkyl. Alternatively, $R_2$ and $R_3$ may be taken together to form either a carbocyclic or heterocyclic ring. $R_4$ is alkyl, arylalkyl, cycloalkylalkyl, heteroarylalkyl, heterocycloalkylalkyl, CN, $COR_5$, $CO_2R_5$ or $CONR_5R_6$. $R_5$ and $R_6$ are each independently H, alkyl, arylalkyl, cycloalkylalkyl, heteroarylalkyl or heterocycloalkylalkyl. Z is O, S or $NR_8$; $R_8$ is H, CN, sulfonamido, $OR_7$, alkyl, cycloalkyl, aryl, arylalkyl, heterocyclyl, heteroaryl or heteroarylalkyl. $R_7$ is H, alkyl, arylalkyl, cycloalkylalkyl, heterocycloalkylalkyl, or heteroarylalkyl.

One preferred embodiment of the instant invention are compounds of formula I, as defined above, wherein $R_1$ is alkyl; $R_2$ is selected from the group consisting of aryl and heteroaryl; $R_3$ is H; $R_4$ is selected from the group consisting of alkyl, arylalkyl, $CO_2R_5$ and $CONR_5R_6$; $R_5$ and $R_6$ are independently selected from the group consisting of H, alkyl and arylalkyl; Z is selected from the group consisting of O, S and $NR_8$; and $R_8$ is selected from the group consisting of H and CN.

In another preferred embodiment, the invention comprises compounds of formula I, as defined above, wherein $R_4$ is selected from the group consisting of alkyl, arylalkyl, $CO_2R_5$ and $CONR_5R_6$.

In yet another preferred embodiment, the instant invention comprises the compounds of formula I, as defined above, wherein $R_4$ is $CO_2R_5$ or $CONR_5R_6$ and Z is O.

In yet a further preferred embodiment, the instant invention comprises the compounds of formula I, as defined above, wherein $R_4$ is selected from the group consisting of alkyl and arylalkyl, and Z is O.

In still yet another preferred embodiment, the instant invention comprises the compounds of formula I, as defined above, wherein $R_1$ is $CH_3$; $R_2$ is aryl; $R_4$ is $CO_2R_5$; $R_5$ is alkyl; and Z is O.

In still yet another preferred embodiment, the instant invention comprises the compounds of formula I, as defined above, wherein $R_1$ is $CH_3$; $R_2$ is aryl; $R_4$ is $CONR_5R_6$; $R_5$ is alkyl, $R_6$ is H; and Z is O.

The invention further provides a pharmaceutical composition comprising a compound of formula I, as defined above, and a pharmaceutically acceptable carrier. Optionally the pharmaceutical composition may further comprise at least one other anti-cancer agent formulated as a fixed dose.

The invention also provides a method for treating a proliferative disease via modulation of the Eg5 motor protein, and/or, inducing apoptosis comprising administering to a mammalian species in need of such treatment an effective amount of at least one compound of formula I, as defined above. In another embodiment, the invention provides a method for treating a proliferative disease via modulation of the Eg5 motor protein comprising administering to a mammalian species in need of such treatment an effective amount of at least one compound of formula L as defined above, in combination (simultaneously or sequentially) with at least one other anti-cancer agent. In a preferred embodiment, the proliferative disease is cancer.

Certain compounds of formula I may generally be prepared according to the following schemes and the knowledge of one skilled in the art. Solvates (e.g., hydrates) of the compounds of formula I are also within the scope of the present invention. Methods of solvation are generally known in the art. Accordingly, the compounds of the instant invention may be in the free or hydrate form, and may be obtained by methods exemplified by the following schemes below.

Scheme I

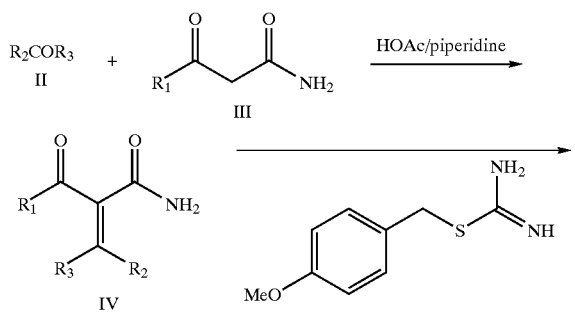

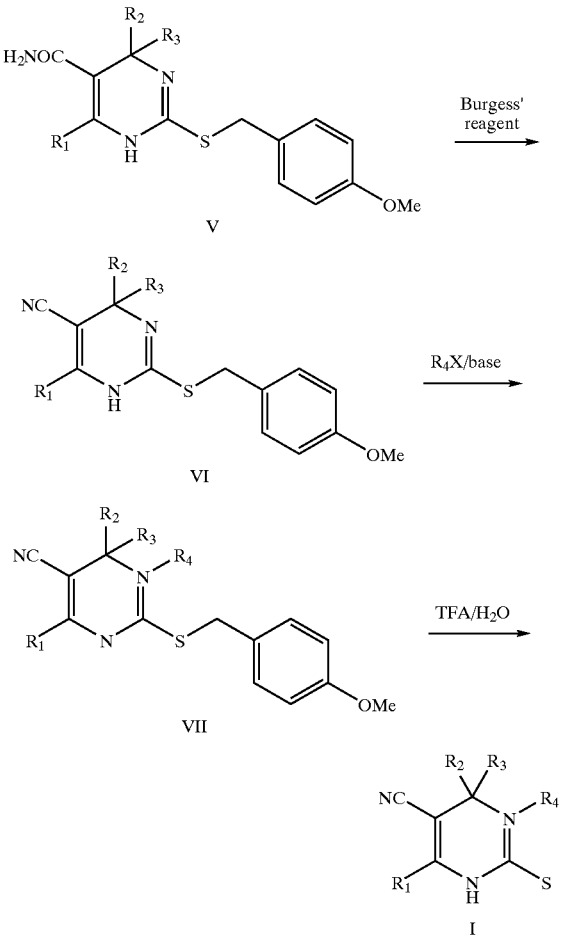

Compounds of formula I where Z is S may be made in accordance with Scheme I. A ketone or an aldehyde I (e.g., benzaldehyde, where $R_2$ is phenyl and $R_3$ is H), is condensed with an acetoacetamide III to give a Knoevenagel product IV as a mixture of isomers. Reaction with S-paramethoxybenzyl thiourea provides the protected dihydropyrimidine thione V. The primary amido group of V is dehydrated to the cyano substituent in VI using a dehydrating agent such as Burgess' reagent (methoxycarbonylsulfamoyl)triethylammonium hydroxide, inner salt. The N3 substituent is introduced by reaction with $R_4X$ where $R_4$ is alkyl or acyl, and X is a leaving group, or where $R_4X$ is an isocyanate or haloformate. The protecting group is removed by treatment with acid in the presence of water to give compounds of formula I where Z is S.

Scheme II

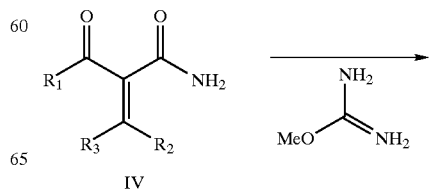

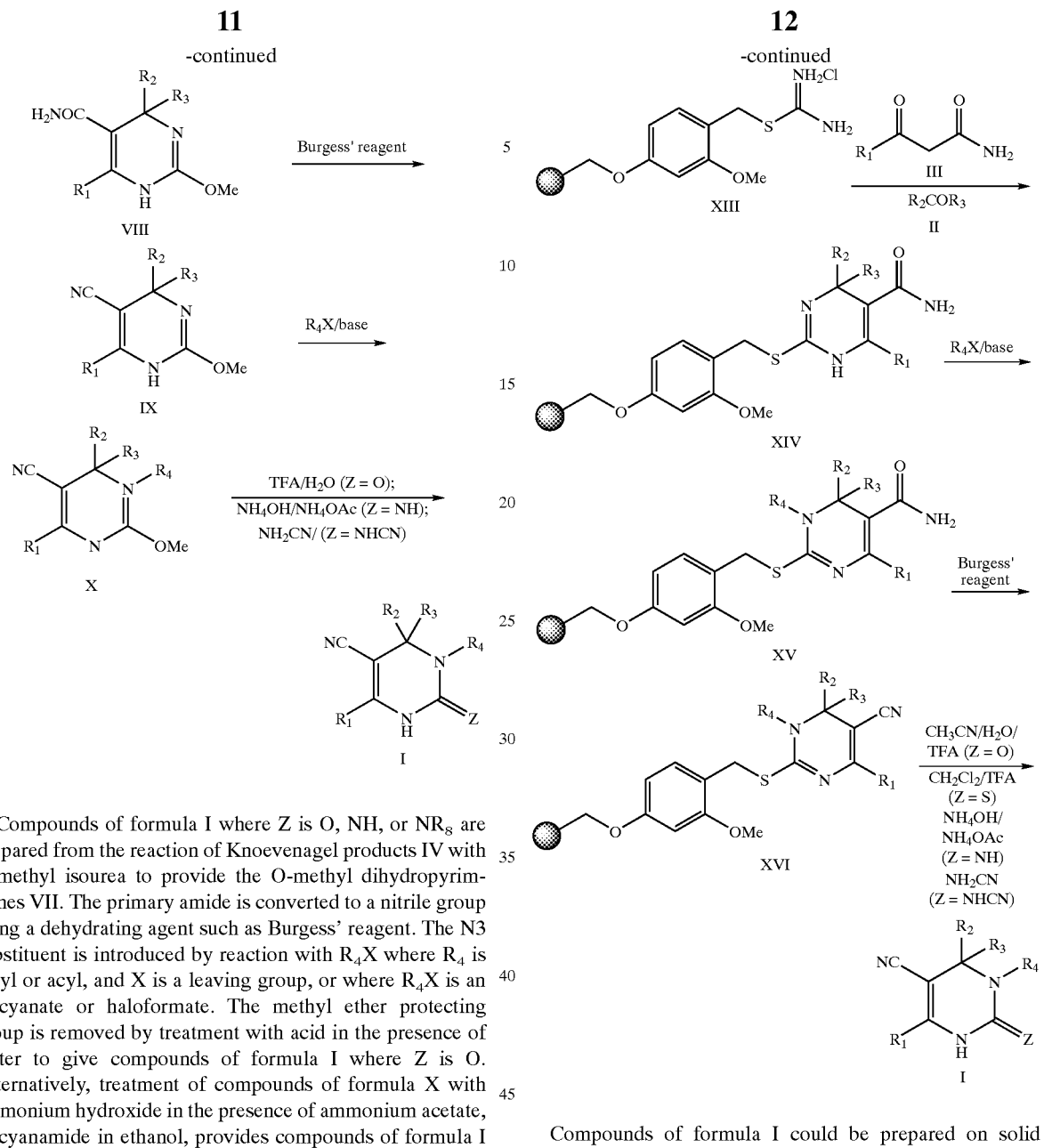

Compounds of formula I where Z is O, NH, or $NR_8$ are prepared from the reaction of Knoevenagel products IV with O-methyl isourea to provide the O-methyl dihydropyrimidines VII. The primary amide is converted to a nitrile group using a dehydrating agent such as Burgess' reagent. The N3 substituent is introduced by reaction with $R_4X$ where $R_4$ is alkyl or acyl, and X is a leaving group, or where $R_4X$ is an isocyanate or haloformate. The methyl ether protecting group is removed by treatment with acid in the presence of water to give compounds of formula I where Z is O. Alternatively, treatment of compounds of formula X with ammonium hydroxide in the presence of ammonium acetate, or cyanamide in ethanol, provides compounds of formula I where Z is NH or $NR_8$.

Compounds of formula I may also be prepared using the Bignelli reaction (D. J. Brown in *The Pyrimidines*, Wiley: New York, 1962, 440).

Scheme III
SOLID PHASE SYNTHESIS

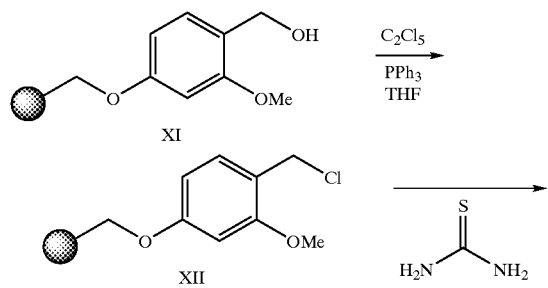

Compounds of formula I could be prepared on solid support as outlined in Scheme III. Starting compound XI denotes a resin-bound benzyl alcohol used for solid support synthesis which is prepared from a Merrifield resin denoted as ●, and 2-methoxy-4-hydroxybenzaldehyde, followed by reduction of the aldehyde with reducing agents such as $NaBH_4$. The benzyl alcohol is converted into the benzyl chloride using agents such as hexachloroethane and triphenylphosphine in THF to form resins of formula XII. The chloride is displaced with thiourea to form the isothiourea resin XIII. The resulting resin is treated with excess of ketoamides like acetoamide (III, $R_1$ is $CH_3$), in the presence of ketones of formula $R_2COR_3$ or aldehydes of formula $R_2CHO$ to form the resin-bound pyrimidinethiones of formula XIV. The N3 substituent is introduced using $R_4X$, where X is a leaving group and $R_4$ is alkyl or acyl, or $R_4X$ is an isocyanate, or haloformate, in the presence of base to form structures of formula XV. The primary amide can be dehydrated to the cyano group using reagents such as Burgess' reagent to form compounds of formula XVI. The products can be cleaved from the resin using a variety of conditions to form compounds of formula I, where Z is determined by the cleavage method employed. Cleavage in the presence of aqueous acid will form compounds of formula I with Z being O, whereas cleavage under anhydrous acid conditions will form compounds of formula I with Z being S. Alternatively, treatment of resins with structure XVI with ammonium hydroxide in the presence of ammonium acetate will form compounds of formula I with Z being NH, while treatment with cyanamide, provides compounds of formula I with Z being NHCN.

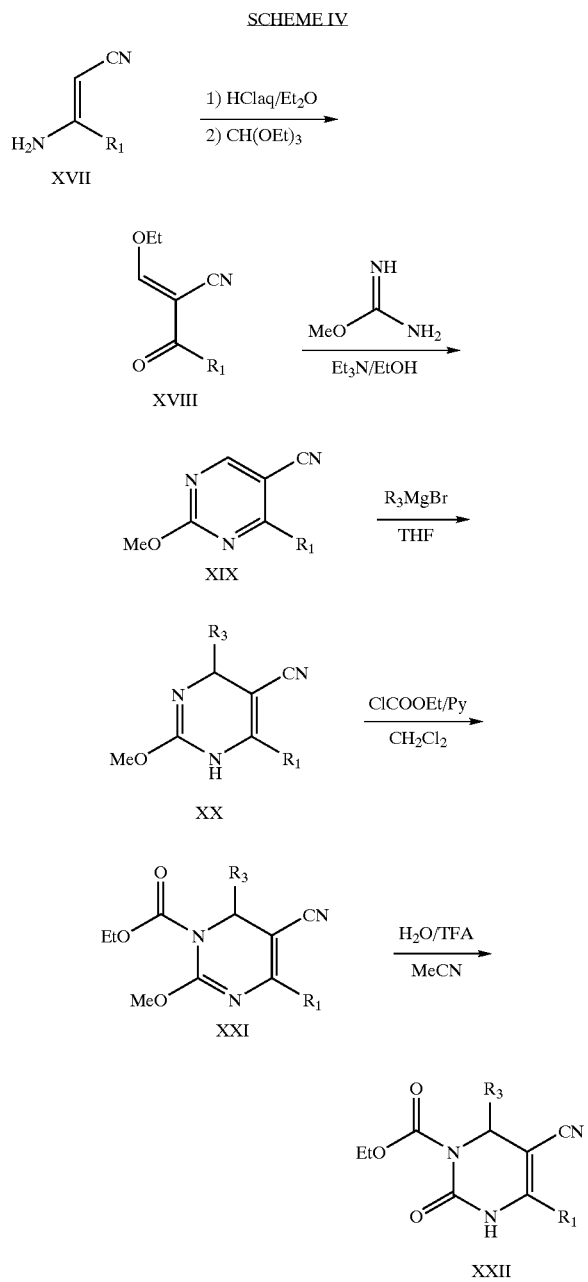

Compounds of formula XVIII may be prepared from a 3-amino-3-alkyl acrylonitrile XVII using the methods illustrated in Scheme IV. Reaction of a compound of formula XVII with aqueous acid, such as hydrochloric acid, followed by treatment with triethyl orthoformate, provides a compound of formula XVIII. Reaction of a compound of formula XVIII with O-methyl isourea in the presence of a base such as triethylamine, provides a pyrimidine of formula XIX. Pyrimidines of formula XIX may be reacted with organometallic species such as a Grignard reagent, $R_3MgBr$, in a solvent such as ether or tetrahydrofuran, to give a pyrimidine of formula XX, which is a compound of formula IX wherein $R_2$ is H. In analogy with Scheme II, a compound of formula XX may be converted into a compound of formula XXII, which is a compound of formula I in which $R_4$ is ethoxycarbonyl and $R_2$ is H.

Alternatively, compounds of formula L wherein Z=O, may be prepared in accordance with Scheme V. Following the procedure of E. H. Hu et al (J. Org. Chem, 1998,63, 3454–3457), a carbonyl compound of formula II is condensed with an acylacetamide of formula III in the presence of urea, cuprous chloride and borontriflouride etherate to give intermediate XXIII. Dehydration with trifluoroacetic anhydride in pyridine affords nitrile XXIV. The N3 substituent is introduced by reaction with $R_4X$ where $R_4$ is alkyl or acyl, and X is a leaving group, or where $R_4X$ is an isocyanate or haloformate to give compounds of formula I. Deprotonation is effected with a base such as sodium hydride or LDA in aprotic solvents such as dimethylformamide or terahydrofuran.

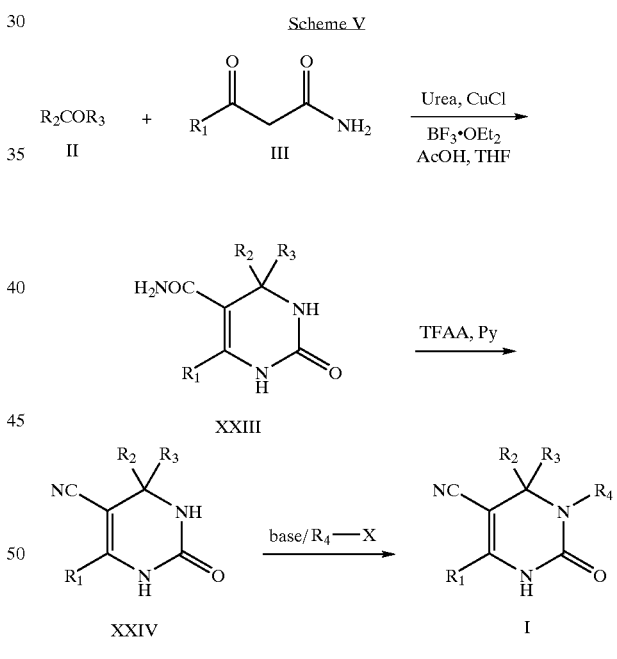

In yet another procedure, compounds of formula I, wherein Z=O, may be prepared in accordance with Scheme VI. A carbonyl compound of formula II is condensed with an acylacetamide of formula m in the presence of urea and polyphospate ester to directly afford nitrile XXIV. Introduction of the N3 substituent follows the procedure as described in Scheme V. Compounds of formula I, where $R_4$ is aminocarbonyl, may also be obtained by first forming a reactive intermediate such as a nitrophenylcarbamate of formula XXV, which is subsequently reacted with an amine.

Scheme VI

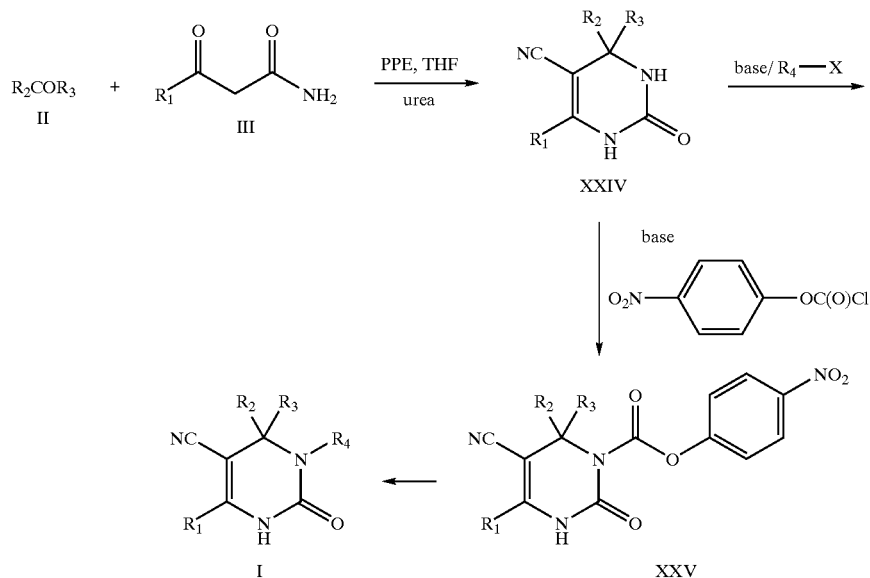

In all of the above schema, a 2-acyl acetonitrile derivative, i.e., $R_1COCH_2CN$, may be substituted for a compound of formula III.

As discussed in the background section, Eg5 is a kinesin-like motor protein that facilitates spindle bipolarity during mitosis of the cell cycle. More specifically, the Eg5 protein acts to sort and bundle microtubules of the mitotic spindle during mitosis. Accordingly, Eg5 participates in cell cycle regulation through the spindle checkpoint during the M phase of the cycle. While not wishing to be bound by any theory, it is believed that the compounds of the instant invention act as Eg5 inhibitors. This is theorized because the compounds of the instant invention induce a monopolar astral array of microtubules (the monoastral phenotype) and it has been shown that when Eg5 activity is absent, the monoastral phenotype forms. Regardless of the mechanism of action, the compounds of the instant invention have been shown to cause disruption of the bipolar spindle, spindle checkpoint initiation, mitotic arrest, programmed cell death and tumor cell proliferation inhibition. Furthermore, the compounds of the invention induce a cell cycle arrest in mitosis that is not transient but rather which progresses into programmed cell death. The compounds also exhibit high potency, inducing mitotic arrest and apoptosis in human cells in vitro at concentrations in the low or sub µM range. Additionally, in contrast to microtubule agents, the compounds do not disrupt the dynamic instability of microtubules. The instant invention may therefore more specifically target the mitotic spindle of proliferating cells, which may provide for different toxicity profiles than those of existing anti-cancer drugs.

The compounds according to the invention have pharmacological properties; in particular, the compounds of formula I induce mitotic arrest and are believed to be Eg5 inhibitors. The novel compounds of formula I are thus useful in the therapy of a variety of proliferative diseases (including but not limited to diseases associated with the Eg5 motor protein) such as cancer, autoimmune diseases, viral diseases, fungal diseases, neurodegenerative disorders and cardiovascular disease.

More specifically, the compounds of formula I are useful in the treatment of a variety of cancers, including, but not limited to, the following:

a) carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

b) hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

c) hematopoietic tumors of myeloid lineage, including acute and chronic myelogenous leukemias, myelodysplastic syndrome and promyelocytic leukemia;

d) tumors of mesenchymal origin, including fibrosarcoma and rhabdomyosarcoma;

e) tumors of the central and peripheral nervous system, including astrocytoma, neuroblastoma, glioma and schwannomas; and f) other tumors, including melanoma, seminoma, teratocarcinoma, osteosarcoma, xenoderoma pigmentosum, keratoctanthoma, thyroid follicular cancer and Kaposi's sarcoma.

Due to the key role of motor proteins in the regulation of cellular proliferation in general, inhibitors could act as reversible cytostatic agents which may be useful in the treatment of any disease process which features abnormal cellular proliferation, e.g., benign prostatic hyperplasia, familial adenomatosis polyposis, neurofibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of formula I induce apoptosis. The apoptotic response is aberrant in a variety of human diseases. Compounds of formula I, as modulators of apoptosis, will be useful in the treatment of cancer (including but not limited to those types mentioned herein above), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of formula I may modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of formula I are useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of formula I may also be useful in inhibiting tumor angiogenesis and metastasis.

The instant invention may also inhibit other motor proteins, for example, including but not limited to: those human motor proteins that correspond to, Xk1p2, MKLP1, CHO1, chromokinesins, Nod, Cenp-E, MCAK, members of the BimC family, and members of the $KaR_3$ family. Additionally, compounds used in the methods of the instant invention may also act as inhibitors of other kinesin or kinesin-like proteins and thus be effective in the treatment of diseases associated with other kinesin or kinesin-like proteins.

The compounds of this invention may also be useful in combination (administered together or sequentially) with known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones; hormonal agents, such as tamoxifen; thymidilate synthase inhibitors, such as 5-fluorouracil; and anti-metabolites, such as methoxtrexate.

If formulated as a fixed dose, such combination products employ the compounds of this invention within the dosage range described below and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

Assays

The pharmacological properties of the compounds of this invention may be confirmed by a number of pharmacological assays. The exemplified pharmacological assays which follow have been carried out with the compounds according to the invention and their salts. The compounds of formula I exhibited antiproliferative activity. Preferred compounds exhibit $IC_{50}$ values less than or equal to about 10 μM.

Cell Culture

Cell lines are maintained in RPMI-1640 plus 10% fetal bovine serum.

72-Hour Proliferation Assay

Cells are plated at a density of 3,000–6,000 cells/well, depending upon the cell line used, in a 96-well plate. The cultures are grown overnight. Cells were then treated in triplicate with a seven concentration dose-response curve. The maximum concentration of DMSO never exceeded 0.5%. Cells were exposed to compound for 72 hours. Proliferation was measured using XTT or MTS from Promega. The ovarian, breast, prostate, lung, leukemia, and colorectal human cancer cell lines used in this assay included but were not limited to, for example, A2780S, SKBR3, MDA-MB-231, PC3, LX-1, K562, HT-29, WiDr, HCT-15 and HCT116. The compounds of formula I exhibited activity in the 72-hour cell proliferation assay, inhibiting cell proliferation in one or more of the cell lines listed above with at an $IC_{50}$ less than or equal to about 10 μM.

Clonogenic Growth Assay

Colony growth inhibition was measured for A2780 ovarian carcinoma cells using a standard clonogenic assay. Briefly, 200 cells/well were seeded into 6-well tissue culture plates (Falcon, Franklin Lakes, N.J.) and allowed to attach for 18 hours. Assay medium consisted of RPMI-1640 plus 10% fetal bovine serum. Cells were then treated in duplicate with a six concentration dose-response curve. The maximum concentration of DMSO never exceeded 0.25%. Cells were exposed to compound for 4, 8 or 24 hours. Compound was then removed and the cells were washed with 2 volumes of PBS. The normal growth medium was then replaced. Colonies were fed with fresh media every third day. Colony number was scored on day 10–14 using a Optimax imaging station. The compound concentration required to inhibit 50% or 90% of colony formation ($IC_{50}$ or $IC_{90}$, respectively) was determined by non-linear regression analysis. The coefficient of variance (SD/mean, n=3)=30%. When exposed to cells for 24 hours, the compounds of formula I exhibited activity in the clonogenecity assay.

Combination Studies—Clonogenic Growth Assays

Combination studies to examine the use of the Eg5 inhibitors of formula I in combination with other antineoplastic agents were conducted essentially the same as the standard colony growth assay with the exception of compound treatment. In the combination studies, the cells were treated with both a compound of formula I and another antineoplastic agent. The compounds were administered simultaneously or sequentially; both the order of sequence and length of treatment (1 to 24 hours) were varied. Data evaluation was based upon the isobologram analysis and the envelope of additivity, using the line of multiplicity which compares the survival fractions of combination treatments with those of single drug treatments.

Cell Cycle Analysis

The cell cycle profile of cells treated with compounds of formula I was monitored by flow cytometry. Briefly, A2780 ovarian carcinoma cells were seeded at a density of $2 \times 10^5$ per well in standard 6 well culture plates and permitted to grow for 17 hours. Cells were then exposed to compounds of formula I at varying concentrations for 2 to 24 hours. Following exposure, cell populations were harvested, stained with propidium iodide to determine DNA content and also stained with the appropriate immunological reagent for protein biomarkers of mitosis and apoptosis, including, for example, anti-phospho-ThreonineProline, anti-M Phase Phospoprotein 2 (MMP2), and anti-p85 PARP. The compounds of formula I exhibited activity in the cell cycle profile analysis assay, producing significant increases in mitotic and apoptotic fractions of the cell population.

Immunocytochemistry Assays

A780 ovarian carcinoma cells or PTK2 kangaroo rat kidney epitheilal cells were plated at a density of 200 to 2000 cells per well in 4 chamber glass slides and allowed to attach overnight. Cells were then treated with compounds of formula I at concentrations of 100 nM to 50 $\mu$M for 4 to 30 hours, fixed and permeabilized for subsequent staining. Stain reagents included, for example, propidium iodide, DAPI, rhodamine phalloidin, anti-$\alpha$tubulin, anti-$\beta$tubulin, anti-$\gamma$tubulin, and the appropriate fluorescent-tagged secondary antibodies. Cells were imaged by fluorescent and confocal fluorescent microscropy. The compounds of formula I inhibited bipolar spindle formation and induced a monoastral array of microtubules.

Further subject matter of the invention also includes pharmaceuticals for use as described above including controlling cancer, inflammation and arthritis, which contain at least one compound of the formula I as defined above or at least one of its pharmacologically acceptable acid addition salts, and the use of a compound of the formula I as defined above for the preparation of a pharmaceutical having activity against proliferative diseases as described previously including against cancer, inflammation and/or arthritis.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

5-Cyano-3,6-dihydro-4-methyl-6-(3-nitrophenyl)-2-thioxo-1-(2H)-pyrimidinecarboxylic acid, 1-ethyl ester A. Step 1

A mixture of 6.42 g of acetoacetamide, 8.0 g of 3-nitrobenzaldehyde, 0.61 ml of acetic acid, and 0.21 ml of piperidine in 30 ml of toluene was heated to reflux. A Dean Stark trap was used to azeotrope the water produced. After refluxed for 2 h, the reaction mixture was cooled to room temperature, with a lot of solid appeared, it was treated with a solution of 300 ml of EtOAc and 25 ml MeOH, the solid was then filtered off, rinsed with 15 ml of EtOAc twice to give 3.1 g of desired product in 25% yield.

B. Step 2

A mixture of 200 mg of the compound of Example 1, Step 1, 198 mg of 2-(4-methoxybenzyl)-2-thiopseudourea HCl salt, 84 mg of sodium acetate in 3.6 ml DMF was heated at 85° C. for 15 h, then cooled to room temperature. The resulting reaction mixture was purified by preparative HPLC using a (YMC S5 ODS 20×100 mm) column, the desired fraction was concentrated to dryness. Saturated NaHCO$_3$ (50 ml) was added and extracted with EtOAc (3×50 ml), combined EtOAc extracts were washed with 30 ml of brine, dried with MgSO$_4$, filtered and concentrated under vacuum to give 126.1 mg desired product in 36% yield.

C. Step 3

A mixture of the compound of Example 1, Step 2 (86.5 mg) and Burgess reagent (150 mg) in 7.0 ml of anhydrous THF was stirred at room temperature for 1 h, concentrated under vacuum, then purified by preparative HPLC using a YMC S5 (ODS 20×100 mm) column to give 80.8 mg of desired product in 87% yield.

D. Step 4

To a solution of the compound of Example 1, Step 3 (60 mg) and pyridine (0.1 ml in 0.6 ml of CH$_2$Cl$_2$, 17 $\mu$l of ethylchloroformate was added, after stirring for 2.5 h, another 22 $\mu$l of ethylchloroformate was added, the reaction mixture was stirred for 2 h, then 0.3 ml of trifluoroacetic acid was added, the resulting mixture was stirred for another 1 h, and concentrated under vacuum, diluted with DMF, MeOH and a little CH$_2$Cl$_2$, filtered, then purified by preparative HPLC using a (YMC S5 ODS 20×100 mm) column to give 22.5 mg of product in 42.7% yield. MS (M–H)$^+$=345. HPLC RT=2.85 min (YMC S5 ODS column 4.6×50 mm, 10–90% aqueous methanol over 4 minutes containing 0.2% phosphoric acid, 4 ml/min, monitoring at 220 nm)

EXAMPLE 2

5-Cyano-3,6-dihydro-4-methyl-6-(3-nitrophenyl)-2-oxo-1-(2H)-pyrimidinecarboxylic acid, 1-ethyl ester A. Step 1

10.92 g of NaHCO$_3$ was added portionwise to a solution of 7.83 g of the compound of Example 1, Step 1 and 7.48 g of o-methylisourea hydrogen sulfate in DMF (100 ml), there was gas evolved. The reaction mixture was stirred for 2 h, then heated at 65° C. overnight, cooled to room temperature, diluted with 800 ml of EtOAc, washed with water (2×100 ml) and brine (1×100 ml). The organic layer was dried MgSO$_4$, filtered and concentrated under vacuum. The resulting residue was triturated in EtOAc-CH$_2$Cl$_2$-hexane to give 5.48 g of desired product as solid (56%).

B. Step 2

A mixture of the compound of Example 2, Step 1 (209 mg) and Burgess reagent (274.5 mg) in CH$_2$Cl$_2$ (5 ml ) and THF (10 ml) was stiff ed overnight. The reaction mixture was concentrated under vacuum, diluted with 150 or of EtOAc, then washed with saturated NaHCO$_3$ (2×30 mm) and brine (1×30 ml), dried with MgSO$_4$, concentrated under vacuum. The resulting residue was purified silica gel chromatography to give 136 mg (69.4%) of desired product.

C. Step 3

1.23 ml of pyridine was added to a solution of 2.075 g of the compound of Example 2, Step 2 in CH$_2$Cl$_2$ (30 ml) under argon at 0° C., then 0.87 ml of ethyl chloroformate was added slowly. The reaction mixture was warmed to room temperature and stirred for 3 h, diluted with a mixture of saturated of NaHCO$_3$ (50 ml) and brine (50 ml), extracted with EtOAc three times, the combined layers were washed with brine and dried with MgSO$_4$, filtered and concentrated under vacuum, purified by silica gel chromatography to give 2.57 g (298% ) of desired product.

D. Step 4

2.5 ml of TFA was added to a solution of 1.44 g of the compound of Example 2, Step 3 in CH$_3$CN (25 ml) and H$_2$O (2.5 ml), the reaction mixture was stirred for 2 h, a lot of white solid appeared. The solid was filtered off, rinsed with CH$_3$CN (3×20 ml) and hexane (2×23 ml), dried in air to give 860 mg (62.2%) desired product. The filtrate was concentrated under vacuum, the solid was recrystallized in CH$_3$CN to give another 320 mg (23.2%) of product. MS (M–H)$^+$= 329. HPLC RT=2.53 min (YMC S5 ODS column 4.6×50 mm, 10–90% aqueous methanol over 4 minutes containing 0.2% phosphoric acid, 4 ml/min, monitoring at 220 nm)

EXAMPLE 3

5-Cyano-3,6-dihydro-4-methyl-6-(3-nitrophenyl)-2-oxo-1-(2H)-pyrimidinecarboxylic acid, 1-ethyl amide.

A. Step 1

To a solution of the compound of Example 2, Step 2 (100 mg; 0.37 mmol) and pyridine (0.74 mmol; 18 µL) in dichloroethane (406 µL) was added 4-nitrophenyl chloroformate (81 mg; 0.40 mmol) and the resulting solution was stirred at room temperature for 1.5 hours. The reaction mixture was diluted with saturated $NaHCO_3$ (30 mL), extracted with ethyl acetate (3×50 mL), dried ($MgSO_4$) and concentrated in vacuo to afford a white foam. Purification by chromatography ($SiO_2$:20% EtOAc/hexane) afforded the desired compound as a colorless foam (99 mg; 62%)

B. Step 2

To a solution of the compound of Example 3, Step 1 (12 mg; 27 µmol) in THF (0.1 mL) was added 2M ethylamine in THF solution (15 µL; 30 µmmol) in one portion at room temperature and the resulting yellow solution was stirred 30 minutes. Dilution of the reaction mixture with methanol (1.8 mL) afforded a yellow solid which was collected by suction filtration and purified by preparative HPLC to afford the title compound as a white solid (20 mg; 22%).

In contrast to the method of Example 2 above, in this case the 2-methoxy group hydrolyzed during isolation and purification to afford the dihydropyrimidinone ring without the need for treatment with TFA (Example 2, Step 4).

EXAMPLE 4

5-Cyano-3,6-dihydro-4-methyl-6-(3-nitrophenyl)-2-oxo-1-(1-oxobutyl)-(2H)-pyrimidine A. Step 1

23.7 µl of butyryl chloride was added to a solution of 52 mg of the compound of Example 2, Step 2 and 0.15 ml of pyridine in 0.6 ml of anhydrous $CH_2Cl_2$, the reaction mixture was stirred for 1 h, then 24 µl of butyryl chloride was added, the reaction was stirred for 1.5 h, purified by preparative HPLC using a YMC S5 (ODS 20×100 mm) column to give 30 mg desired product.

B. Step 2

A solution of 30 mg of the compound of Example 4, Step 1, 0.2 ml of $H_2O$ and 0.2 ml of TEA in 1.2 ml $CH_3CN$ was stirred for 1.5 h, it was added another 0.1 ml of TFA and stirred for another 2.5 h. The reaction mixture was concentrated under vacuum, and purified by preparative HPLC using a YMC S5 (ODS 20×100 mm) column to give 11.8 mg desired product. MS $(M-H)^+=327$. HPLC RT=3.06 min (YMC S5 ODS column 4.6×50 mm, 10–90% aqueous methanol over 4 minutes containing 0.2% phosphoric acid, 4 ml/min, monitoring at 220 nm)

EXAMPLE 5

Enantio 5-Cyano-3,6-dihydro-4-methyl-6-(3-nitrophenyl)-2-oxo-1-(2H)-pyrimidinecarboxylic acid, 1-ethyl ester (Enantiomer A)

53 mg of the compound of Example 2, Step 4 was dissolved in absolute EtOH, preparative chiral separation was carried out using a Chiralcel OD-H S5 (4.6×250 mm) column, 20 mg of enantiomer A and 27 mg of enantiomer B were obtained. MS $(M-H)^+=329$. HPLC-Chiral RT=10.44 min (Chiralcel OD-H, S5, column 4.6×250 mm, 10% MeOH/10% EtOH/Heptane, 1.0 ml/min, monitoring at 220 nm, 94.7% ee)

EXAMPLE 6

Enantio 5-Cyano-3,6-dihydro-4-methyl-6-(3-nitrophenyl)-2-oxo-1-(2H)-pyrimidinecarboxylic acid, 1-ethyl ester (Enantiomer B)

MS $(M-H)^+=329$. HPLC-Chiral RT=12.92 min (Chiralcel OD-H, S5, column 4.6×250 mm, 10% MeOH/10% EtOH/Heptane, 1.0 ml/min, monitoring at 220 nm, 99.64% ee)

EXAMPLE 7

5-Cyano-3,6-dihydro-4-methyl-6-(3-aminophenyl)-2-oxo-1-(2H)-pyrimidinecarboxylic acid, 1-ethyl ester A solution of 12 mg of the compound of Example 1, Step 4 in ethanol was treated with 100 mg of tin (II) chloride and heated to reflux under argon for 90 min., the reaction was cooled down and quenched with saturated $NaHCO_3$ solution and extracted with EtOAc (3×50 ml). The combined organic layer was washed with $H_2O$, dried with $Na_2SO_4$ and concentrated under vacuum. It was triturated with hexane and ether to give 8 mg of crude product, which was further purified by preparative HPLC to afford 3 mg of desired product as TFA salt. MS $(M+H)^+=301$. HPLC RT=1.685 min (YMC S5 ODS column 4.6×50 mm, 10–90% aqueous methanol over 4 minutes containing 0.1% of TFA, 4 ml/min, monitoring at 220 nm)

EXAMPLE 8

5-Cyano-3,6-dihydro-4-methyl-6-(3-(N,N-dimethyl)aminophenyl)-2-oxo-1-(2H)-pyrimidinecarboxylic acid, 1-ethyl ester A solution of 12 mg of the compound of Example 7 in $CH_3CN$ (1 ml) was added paraformaldehyde (40 mg), sodium cyanoborohydride (30 mg) followed by 2 drops of acetic acid. The reaction mixture was stirred at room temperature for 2 h, then quenched with saturated $NaHCO_3$ solution and extracted with EtOAc three times. The combined organic layer was washed with brine, dried with $Na_2SO_4$ and concentrated under vacuum. The resulting residue was purified by preparative HPLC to yield 3.2 mg of desired product as TFA salt. MS $(M+H)^+=329$. HPLC RT=1.76 min (YMC S5 ODS column 4.6×50 mm, 10–90% aqueous methanol over 4 minutes containing 0.1% of TFA, 4 ml/min, monitoring at 220 nm)

Examples 9 through 15 were prepared using the methods of Example 2 with the substitution of an appropriate benzaldehyde in Step 1.

EXAMPLE 9

5-Cyano-3,6-dihydro-4-methyl-6-(3-trifluoromethylphenyl)-2-oxo-1-(2H)-pyrimidinecarboxylic acid, 1-ethyl ester HPLC-HI 100% at 2.84 min (YMC S5 ODS column 4.6×50 mm, 10–90% aqueous methanol over 4 minutes containing 0.1% of TFA, 4 ml/min, monitoring at 220 nm). MS: $[M+H]^+=354$.

EXAMPLE 10

5-Cyano-3,6-dihydro-4-methyl-6-(2,3-dichlorophenyl)-2-oxo-1-(2H)-pyrimidinecarboxylic acid, 1-ethyl ester HPLC-HI 100% at 3.2 min (YMC S5 ODS column 4.6×50 mm, 10–90% aqueous methanol over 4 minutes containing 0.1% of TFA, 4 ml/min, monitoring at 220 nm). MS: [M−H]⁻=352.

EXAMPLE 11

5-Cyano-3,6-dihydro-4-methyl-6-(3-methoxyphenyl)-2-oxo-1-(2H)-pyrimidinecarboxylic acid, 1-ethyl ester HPLC-HI 100% at 2.42 min (YMC S5 ODS column 4.6×50 mm, 10–90% aqueous methanol over 4 minutes containing 0.1% of TFA, 4 ml/min, monitoring at 220 nm). MS: [M+H]⁺=316.

EXAMPLE 12

5-Cyano-3,6-dihydro-4-methyl-6-(3,5-dichlorophenyl)-2-oxo-1-(2H)-pyrimidinecarboxylic acid, 1-ethyl ester HPLC-HI 87% at 3.26 min (YMC S5 ODS column 4.6×50 mm, 10–90% aqueous methanol over 4 minutes containing 0.1% of TFA, 4 ml/min, monitoring at 220 nm). MS: [M−H]⁻=352.

EXAMPLE 13

5-Cyano-3,6-dihydro-4-methyl-6-(3,4-dichlorophenyl)-2-oxo-1-(2H)-pyrimidinecarboxylic acid, 1-ethyl ester HPLC-HI 100% at 3.197 min (YMC S5 ODS column 4.6×50 mm, 10–90% aqueous methanol over 4 minutes containing 0.1% of TFA, 4 ml/min, monitoring at 220 nm). MS: [M−H]⁻=352.

EXAMPLE 14

5-Cyano-3,6-dihydro-4-methyl-6-(3-cyanophenyl)-2-oxo-1-(2H)-pyrimidinecarboxylic acid, 1-ethyl ester HPLC-HI 93% at 2.32 min (YMC S5 ODS column 4.6×50 mm, 10–90% aqueous methanol over 4 minutes containing 0.1% of TFA, 4 m/min, monitoring at 220 nm). MS: [M+H]⁺=311.

EXAMPLE 15

5-Cyano-3,6-dihydro-4-methyl-6-(4-methoxyphenyl)-2-oxo-1-(2H)-pyrimidinecarboxylic acid, 1-ethyl ester HPLC-HI 100% at 2.55 min (YMC S5 ODS column 4.6×50 mm, 10–90% aqueous methanol over 4 minutes containing 0.1% of TFA, 4 ml/min, monitoring at 220 nm). MS: [M+H]⁺=316.

EXAMPLE 16

5-Cyano-3,6-dihydro-4-methyl-6-(4-methylphenyl)-2-oxo-1-(2H)-pyrimidinecarboxylic acid, 1-ethyl ester A. Step 1

A cloudy solution of 3-aminocrotononitrile (41 g, 0.5 mol) in Et₂O (500 ml) was added dropwise to the 15% HCl solution (115 ml) at 0° C. over 30 min with vigorous stirring, and the reaction mixture was stirred at 0° C. for 15 min. The aqueous solution was then separated, extracted with Et₂O (2×125 ml), the combined organic phases dried with Na₂SO₄. Triethyl orthoformate (83 ml) in a 500 ml three-neck flask equipped with addition funnel and distillation set was stirred in 60° C.–65° C. oil bath, the above ether solution was added dropwise such that the rate of addition was equal to the rate of distillation. An additional 83 ml of triethyl orthoformate was added to the reaction when the addition of the ether solution was half complete, the oil bath temperature was slowly raised to 120° C., and the reaction mixture was then stirred for 5 h. Distillation gave 26.6 g (38%) of desired red solid product at 150–155° C./2 mm Hg.

B. Step 2

To a mixture of O-methylisourea sulfate (9.9 g, 80 mmol), the compound of Example 16, Step 1 (7.4 g, 53 mmol) and ethanol (90 ml) was added Et₃N (11 ml, 80 mmol). The mixture was stirred at room temperature for 15 min, then stirred at 66° C. for 3 h, and concentrated to remove EtOH. EtOAc (80 ml) and H₂O (80 ml) were added, the aqueous layer were separated and extracted with EtOAc (2×80 ml), the combined organic layer were dried with Na₂SO₄, concentrated to give brown solid, which was dissolved in EtOAc, filtered through a silica gel pad, washed with EtOAc/heptane (1/1) to remove dark color, and the combined filtrate was concentrated. The solid thus obtained was recrystallized in heptane/EtOAc to give yellow crystal 5.18 g in 65% yield.

C. Step 3

A solution of p-tolylmagnesium bromide in ether (1M, 1 ml, 1 mmol) was added dropwise to a solution of the compound of Example 16, Step 2 (75 mg, 0.5 mmol) in THF (2 ml) at 0° C. under argon. The reaction mixture was stirred at the temperature for 1.5 h, another 3 ml of Grignard reagent was added at −78° C., the reaction was slowly warmed to room temperature and stirred for 2 min. Saturated NH₄Cl (5 ml) and H₂O (5 ml) were added, the mixture was extracted with EtOAc (2×15 ml), the combined organic layer was dried, concentrated and chromatographed on silica gel to give 45.6 mg of desired product in 91% yield.

D. Step 4

To a solution of the compound of Example 16, Step 3 (109 mg, 0.45 mmol) was added pyridine (0.2 ml, 2.5 mmol) in dry CH₂Cl₂ (5 ml) followed by ethyl chloroformate (0.1 ml, 1.05 mmol), and the resulting reaction mixture was stirred at room temperature overnight. MeOH was added, the resulting mixture was stirred for 15 min, concentrated, and chromatographed on silica gel column to give 100 mg desired product as colorless oil (71%).

E. Steps

A mixture of the compound of Example 15, Step 4 (100 mg, 0.32 mmol), H₂O (0.7 ml), CH₃CN (0.5 ml) and TFA (7 ml) was stirred at room temperature for 2 h. The solution was then concentrated to remove CH₃CN, saturated NaHCO₃ was added to make the mixture basic, the white solid precipitate was filtered, washed with H₂O, and dried to give the desired product (64 mg). The crude product was dried and recrystallized from EtOH/H₂O to give another 20 mg desired product as white solid. MS (M+H)⁺=300. HPLC RT=3.40 min (YMC S5 ODS column 4.6×50 mm, 10–90% aqueous methanol over 4 minutes containing 0.2% phosphoric acid, 4 ml/min, monitoring at 220 nm)

EXAMPLE 17

5Cyano-3,6-dihydro-4-methyl-6-cyclohexyl-2-oxo-1-(2H)-pyrimidinecarboxylic acid, 1-ethyl ester To a solution of the compound of Example 16, Step 2 (30 mg, 0.2 mmol) in THF (1.2 ml) was added cyclohexylmagnesium chloride (2 M in ether, 1.0 ml, 2 mmol) at −44° C. under argon, the reaction was slowly warmed to room temperature, and stirred to for 10 min. Saturated NH₄Cl was added, the resulting mixture was extracted several times with EtOAc, the combined organic layer dried, filtered through a silica gel pad, and concentrated to give yellow oil. The oil was dissolved in CH₂Cl₂ (2 ml), then pyridine (80 µl, 0.9 mmol) and ethyl chloroformate (50 µl, 0.5 mmol) were added, the mixture was stirred at room temperature for 30 min, stirred for another 10 min after which H₂O (25 µl) and EtOAc were added, and the mixture dried over Na₂SO₄, filtered through a silica gel pad, and concentrated to give yellow oil. The oil was dissolved in CH₃CN (2 ml), H₂O (0.3 ml) and TFA (0.2 ml) were added, and the mixture stirred at room temperature for 2 h. Saturated NaHCO₃ solution and EtOAc were added, the aqueous layer was separated and extracted with EtOAc, and the combined organic layer was dried over Na₂SO₄, concentrated and chromatographed on silica gel to give 35 mg of desired product as yellow foam (60%). MS (M+H)⁺=392. HPLC RT=3.60 min (YMC S5 ODS column 4.6×50 mm, 10–90% aqueous methanol over 4 minutes containing 0.2% phosphoric acid, 4 ml/min, monitoring at 220 nm)

EXAMPLE 18

5-Cyano-3,6-dihydro-4-methyl-6-phenyl-2-oxo-1-(2H)-pyrimidinecarboxylic acid, 1-ethyl ester To a solution of the compound of Example 16, Step 2 (55 mg, 0.37 mmol) in dry THF (2 ml) was added phenylmagnesium bromide (2 M in THF, 2 ml, 4 mmol) dropwise at −78° C. under argon. After addition, the reaction was slowly warmed to room temperature and stirred for about 10 min, until starting material disappeared. Saturated NH₄Cl solution and H₂O were added, the mixture was extracted with EtOAc for two times, and the combined organic layer was dried over Na₂SO₄, concentrated and chromatographed on silica gel to give solid intermediate. The solid was dissolved in CH₂Cl₂ (5 ml), pyridine (0.15 ml, 1.8 mmol) and ethyl chloroformate (0.1 ml, 1 mmol) were added, and the reaction mixture was stirred at room temperature for 0.5 h. The reaction was quenched with 50 µl of H₂O, diluted with 5 ml of EtOAc, the resulting mixture was dried over Na₂SO₄, filtered through silica gel column to give the intermediate as an oil. The oil was dissolved in CH₃CN (5 ml), H₂O (0.5 ml) and TFA (0.4 ml) were added, the reaction mixture stirred for 1.5 h, and concentrated in vacuo. Saturated NaHCO₃ solution was added to neutralize the mixture, and the precipitate was then filtered and air dried. Recrystallization in EtOAc/heptane to give 70 mg solid product in 66% yield. MS (M+H)⁺=286. HPLC RT=1.28 min. (Phenom-Prime S5 C18 4.6×30 mm, 10–90% aqueous methanol over 2 minutes containing 0.1% TFA, 5 ml/min, monitoring at 220 nm)

Examples 19 through 24 were prepared using the method of Example 18 with the substitution of an appropriate arylmagnesiumhalide.

EXAMPLE 19

5-Cyano-3,6-dihydro-4-methyl-6-(2-methylphenyl)-2-oxo-1-(2H)-pyrimidinecarboxylic acid, 1-ethyl ester MS (M+H)⁺=300. HPLC RT=1.41 min. (Phenom-Prime S5 C18 4.6×30 mm, 10–90% aqueous methanol over 2 minutes containing 0.1% TFA, 5 ml/min, monitoring at 220 nm)

EXAMPLE 20

5-Cyano-3,6-dihydro-4-methyl-6-(3-chlorophenyl)-2-oxo-1-(2H)-pyrimidinecarboxylic acid, 1-ethyl ester MS (M+H)⁺=320. HPLC RT=1.43 min. (Phenom-Prime S5 C18 4.6×30 mm, 10–90% aqueous methanol over 2 minutes containing 0.1% TFA, 5 ml/min, monitoring at 220 nm)

EXAMPLE 21

5-Cyano-3,6-dihydro-4-methyl-6-(3-fluorophenyl)-2-oxo-1-(2H)-pyrimidinecarboxylic acid, 1-ethyl ester MS (M+H)⁺=304. HPLC RT=1.29 min. (Phenom-Prime S5 C18 4.6×30 mm, 10–90% aqueous methanol over 2 minutes containing 0.1% TFA, 5 ml/min, monitoring at 220 nm)

EXAMPLE 22

5-Cyano-3,6-dihydro-4-methyl-6-(4-chlorophenyl)-2-oxo-1-(2H)-pyrimidinecarboxylic acid, 1-ethyl ester MS (M+H)⁺=320. HPLC RT=1.44 min. (Phenom-Prime S5 C18 4.6×30 mm, 10–90% aqueous methanol over 2 minutes containing 0.1% TFA, 5 ml/min, monitoring at 220 nm)

EXAMPLE 23

5-Cyano-3,6-dihydro-4-methyl-6-(4-fluorophenyl)-2-oxo-1-(2H)-pyrimidinecarboxylic acid, 1-ethyl ester MS (M+H)⁺=304. HPLC RT=3.21 min (YMC S5 ODS column 4.6×50 mm, 10–90% aqueous methanol over 4 minutes containing 0.2% phosphoric acid, 4 ml/min, monitoring at 220 nm)

EXAMPLE 24

5-Cyano-3,6-dihydro-4-methyl-6-(2-fluorophenyl)-2-oxo-1-(2H)-pyrimidinecarboxylic acid, 1-ethyl ester MS (M+H)⁺=304. HPLC RT=3.05 min (YMC S5 ODS column 4.6×50 mm, 10–90% aqueous methanol over 4 minutes containing 0.2% phosphoric acid, 4 ml/min, monitoring at 220 nm)

EXAMPLE 25

6-(3,5-Bis-trifluoromethylphenyl)-5-cyano-4-methyl-2-oxo-3,6-dihydro-2H-pyrimidine-1-carboxylic acid ethyl ester A. Step 1

4-(3,5-Bis-trifluoromethylphenyl)-6-methyl-2-oxo-1,2,3,4-tetrahydropyrimidine-5-carboxylic acid amide. A mixture of 3,5-bis(trifluoromethyl)benzaldehyde (2.42 g, 10.0 mmol), acetoacetamide (1.01 g, 10.0 mmol), urea (0.90 g, 15.0 mmol), copper chloride (0.1 g, 1.0 mmol), boron trifluoride etherate (0.09 mL), AcOH (0.04 mL), and THF (20 mL) was heated at 65° C. for 18 h and cooled to room temperature. The resulting precipitates were collected by vacuum filtration, washed with THF, and air dried to give the title compound as an off-white solid(1.33 g, 36%).

B. Step 2

4-(3,5-Bis-trifluoromethylphenyl)-6-methyl-2-oxo-1,2,3,4-tetrahydro-pyrimidine 5-carbonitrile. To a mixture of compound from Step 1 (1.10 g, 3.0 mmol) and pyridine (12 mL) at 0° C. was added trifluoroacetic anhydride (1.3 mL, 9.0 mmol) slowly over 10 min. The reaction mixture became a clear brown solution and was stirred for 18 h, then poured into water. The resulting off-white precipitates were collected by vacuum filtration, washed with water, and air dried to give the title compound as a light brown solid (1.06 g, 100%).

C. Step 3

6-(3,5-Bis-trifluoromethylphenyl)-5-cyano-4-methyl-2-oxo-3,6-dihydro-2H-pyrimidine-1-carboxylic acid ethyl ester. To a solution of compound from Step 2 (60.0 mg, 0.17 mmol) in THF (2 mL) chilled to −78° C. was added LDA (0.15 mL, 0.30 mmol, 2.0 M in hexanes). The resulting mixture was stirred at −78° C. for 15 min, warmed to −25° C. for 15 min, recooled to −78° C. and ethyl chloroformate (20 µL, 0.20 mmol) was added via a syringe. The reaction mixture was stirred at −78° C. for 15 min, gradually warmed to room temperature and stirred for 1 h, quenched with MeOH and concentrated in vacuo. The residue was purified by preparative HPLC (methanol/water); product fractions were combined and concentrated in vacuo to afford the title compound as an off-white solid (28.4 mg, 40%).

$^1$H-NMR (DMSO-$d_6$, 400 MHz): δ 10.64 (s, 1 H), 8.19 (s, 1 H), 7.93 (s, 2 H), 6.15 (s, 1 H), 4.17 (m, 2 H), 2.10 (s, 3 H), 1.17 (t, 3 H, J=7.0 Hz). LC/MS (ES+) 444 (M+Na)$^+$.

EXAMPLE 26

6-Butyl-5-cyano-4-methyl-2-oxo-3,6-dihydro-2H-pyrimidine-1-carboxylic acid ethyl ester A. Step 1

4-Hexyl-6-methyl-2-oxo-1,2,3,4-tetrahydropyrimidine-5-carbonitrile. Polyphosphate ester (1.15 g, 3.89 mmol, 0.30 eq) was added to a sealed tube containing a solution of urea (1.17 g, 19.4 mmol), valeraldehyde (1.38 ml, 12.9 mmol) and acetoacetamide (1.31 g, 12.9 mmol) in THF (15 mL) under argon and heated at 75° C. for three hours. The reaction mixture was cooled to room temperature, polyphosphate ester (8.80 g, 29.8 mmol) was added and the reaction mixture was heated at 85° C. for four hours. The reaction mixture was cooled to room temperature and poured on ice. The aqueous solution was neutralized with 1N NaOH and extracted with chloroform (3×100 mL). The combined organic layers were dried (Na$_2$SO$_4$), filtered and concentrated under vacuum to give the title compound (0.940 g, 97%): HRMS 192.1143 (M−H)$^−$. The product was used in the next step without further purification.

B. Step 2

6-Butyl-5-cyano-4-methyl-2-oxo-3,6-dihydro-2H-pyrimidine-1-carboxylic acid ethyl ester. LDA (0.585 mL. 1.17 mmol, 2.0 M in hexane) was added dropwise to a solution of compound from Step 1 (0.150 g, 0.777 mmol) in THF (5 mL) at −78° C. The reaction mixture was stirred at −78° C. for twenty minutes and ethyl chloroformate (0.111 mL, 1.17 mmol) was added in one portion. The reaction mixture was allowed to warm to room temperature and was stirred for sixteen hours. The reaction mixture was quenched with saturated ammonium chloride (35 ml) and the solution was extracted with chloroform (3×100 ml). The combined organic layers were dried (Na$_2$SO$_4$), filtered and concentrated under vacuum. The residue was purified by flash chromatography (eluting 2/1 ethyl acetate/hexanes) to afford the title compound (0.110 g, 53%) as a solid.

$^1$H-NMR (DMSO-$d_6$, 400 MHz): δ 0.86 (t, 3 H, J=6.79), 1.21–1.33 (m, 7H), 1.54–1.65 (m, 2H), 2.04 (s, 3H), 4.17–4.23 (m, 2H), 4.68 (t, 1H, J=6.42), 10.33 (s, 1H). MS 264 (M−H)$^−$. HRMS 266.1506 (M+H)$^+$.

EXAMPLE 27

5Cyano-4-methyl-6-(3-nitrophenyl)-2-oxo-3,6-dihydro-2H-pyrimidine-1-carboxylic acid methylamine A. Step 1

5-Cyano-4-methyl-6-(3-nitrophenyl)-2-oxo-3,6-dihydro-2H-pyrimidine-1-carboxylic acid 4-nitrophenyl ester. To a suspension of 6-Methyl-4-(3-nitrophenyl)-2-oxo-1,2,3,4-tetrahydro-pyrimidine-5-carbonitrile (0.43 g, 1.7 mmol, prepared by the method described in Example 26, Step 1, in 77% yield) in THF (15 mL) at −78° C. was added LDA (1.25 mL, 2.5 mmol, 2.0 M in hexanes). The resulting mixture was stirred at −78° C. for 15 min, warmed to −25° C. for 15 min, recooled to −78° C. and 4-nitrophenyl chloroformate (0.50 g, 2.5 mmol) was added in one portion. The reaction mixture was stirred at −78° C. for 15 min, gradually warmed to room temperature, quenched with water and extracted with ethyl acetate. The organic extract was washed with brine, dried (MgSO$_4$) and concentrated in vacuo. The residue was purified by flash column chromatography on silica gel using 50% to 70% ethyl acetate-hexane as eluant to give the title compound as a light yellow solid (0.38 g, 53%).

B. Step 2

5-Cyano-4-methyl-6-(3-nitrophenyl)-2-oxo-3,6-dihydro-2H-pyrimidine-1-carboxylic acid methylamide. To a solution of compound from Step 1 (12.5 mg, 0.03 mmol) in THF (1 mL) was added methylamine (4.1 uL, 0.033 mmol, 8 M in EtOH). The reaction mixture was stirred for 2 h and concentrated in vacuo. The residue was purified by preparative HPLC (methanol/water). Product fractions were combined, concentrate in vacuo and lyophilized to give the title compound as a colorless solid (8.2 mg, 87%).

$^1$H-NMR (MeOH-$d_4$, 400 MHz): δ 8.22 (m, 1 H), 8.17 (t, 1 H, J=1.8 Hz), 7.76 (m, 1 H), 7.65 (t, 1 H, J=7.9 Hz), 6.30 (s, 1 H), 2.82 (s, 3 H), 2.18 (s, 3 H). LC/MS (ES+) 338 (M+Na)$^+$.

EXAMPLE 28

5-Cyano-4-methyl-2-oxo-6-phenyl-3,6-dihydro-2H-pyrimidine-1-carboxylic acid ethylamide To a solution 6-Methyl-2-oxo-4-phenyl-1,2,3,4-tetrahydropyrimidine-5-carbonitrile (100 mg, 0.47 mmole, obtained in 65% yield by the procedure described in Example 26, Step 1) in 4 mL of tetrahydrofuran under argon at room temperature was added oil free sodium hydride (17 mg, 0.70 mmole). After stirring for ten minutes, ethyl isocyanate (50 mg, 0.70 mmole) was added. The reaction mixture was diluted with ethyl acetate and washed with dilute citric acid, water and saturated brine. The dried (anhydrous magnesium sulfate) organic extract was concentrated in vacuo and the product purified by flash chromatography on silica gel, eluting with ethyl acetate/hexanes (3:2) to give 100 mg (75%) of title compound as a white solid.

$^1$H-NMR (DMSO-$d_6$, 400 MHz) δ 10.51 (br s, 1 H); 8.79 (t, J=5.4 Hz, 1 H); 7.22–7.48 (m, 5 H); 6.09 (s, 1 H); 3.10–3.25 (m, 2 H); 2.08 (s, 3 H); 1.03 (t, J=7.2 Hz, 3 H). LC/MS (ES+) 285 (M+H)$^+$.

EXAMPLE 29

5-Cyano-6-(3,5-dichlorophenyl)-4-methyl-2-oxo-3,6-dihydro-2H-pyrimidine-1-carboxylic acid 2-methoxy-ethyl ester Using 3,5-dichlorobenzaldehyde and following the procedure described in Example 2, the title compound was obtained in 3% overall yield.

$^1$H-NMR (DMSO-$d_6$, 500 MHz): δ 10.59 (s, 1 H), 7.66 (t, 1 H, J=1.6 Hz), 7.31 (d, 2 H, J=1.6 Hz), 5.90 (s, 1 H), 4.26 (m, 2 H), 3.54 (m, 2 H), 3.25 (s, 3 H), 2.11 (s, 3 H). LC/MS (ES+) 384 (M+H)$^+$.

EXAMPLE 30

5-Cyano-4-methyl-2-oxo-6-(3-trifluoromethylphenyl)-3,6-dihydro-2H-pyrimidine-1-carboxylic acid ethylamide Using 3-trifluoromethylbenzaldehyde and following a modification of the procedure described in Example 2, the title compound was obtained in 3% overall yield.

$^1$H-NMR (CDCl$_3$, 400 MHz): δ 8.68 (s, 1 H), 7.60 (m, 2 H), 7.53 (m, 2 H), 6.37 (s, 1 H), 3.30 (m, 2 H), 2.08 (s, 3 H), 1.17 (t, 3 H, J=7.0 Hz). LC/MS (ES+) 353 (M+H)$^+$, 375 (M+Na)$^+$.

EXAMPLE 31

5-Cyano-46-(3,5-dichlorophenyl)-4-methyl-2-oxo-3, 6-dihydro-2H-pyrimidine-1-carboxylic acid ethylamide Using 3,5-dichlorobenzaldehyde and following a modification of the procedure described in Example 2, the tide compound was obtained in 7% overall yield.

$^1$H-NMR (DMSO-d$_6$, 400 MHz): δ 10.56 (s, 1 H), 8.76 (t, 1 H, J=5.3 Hz), 7.63 (t, 1 H, J=1.8 Hz), 7.27 (d, 2 H, J=1.8 Hz), 6.10 (s, 1 H), 3.16 (m, 2 H), 2.09 (s, 3 H), 1.03 (t, 3 H, J=7.0 Hz). LC/MS (ES+) 353 (M+H)$^+$, 375 (M+Na)$^+$.

EXAMPLE 32

3-Butyryl-4-(3,5-dichlorophenyl)-6-methyl-2-oxo-1, 2,3,4-tetrahydropyrimidine-5-carbonitrile Using 3,5-dichlorobenzaldehyde and following the procedure described in Example 2, the title compound was obtained in 7% overall yield.

$^1$H-NMR (DMSO-d$_6$, 500 MHz): δ 10.63 (s, 1 H), 7.63 (t, 1 H, J=1.6 Hz), 7.26 (d, 2 H, J=1.6 Hz), 6.04 (s, 1 H), 2.95 (m, 1 H), 2.74 (m, 1 H), 1.54 (m, 2H), 2.11 (s, 3 H), 0.86 (t, 3 H, J=7.1 Hz).

EXAMPLE 33

5-Cyano-4-methyl-2-oxo-6-(3-trifluoromethylphenyl)-3,6-dihydro-2H-pyrimidine-1-carboxylic acid (2-dimethylamino-ethyl)-amide Using 3-trifluoromethylbenzaldehyde and following the procedure described in Example 2, the title compound was obtained in 8% overall yield.

$^1$H-NMR (MeOH-d$_4$, 400 MHz): δ 7.64 (m, 1 H), 7.59 (m, 3 H), 6.25 (s, 1 H), 3.43 (m, 1 H), 3.38 (m, 1 H), 2.56 (t, 1 H, J=6.2 Hz), 2.32 (s, 6 H), 2.15 (d, 3 H, J=0.9 Hz); LC/MS (ES+) 396 (M+H)$^+$.

EXAMPLE 34

5-Cyano-4-methyl-2-oxo-6-(3-trifluoromethylphenyl)-3,6-dihydro-2H-pyrimidine-1-carbothioic acid S-ethyl ester Using 3-trifluoromethylbenzaldehyde and following a modification of the procedure described in Example 2, the title compound was obtained in 3% overall yield.

$^1$H-NMR (CDCl$_3$, 400 MHz): δ 8.21 (s, 1 H), 7.61 (m, 1 H), 7.52 (m, 3 H), 6.24 (s, 1 H), 2.87 (m, 2 H), 2.26 (d, 3 H, J=0.9 Hz), 1.26 (t, 3 H, J=7.5 Hz). LC/MS (ES+) 392 (M+Na)$^+$.

EXAMPLE 35

5-Cyano-4-methyl-2-oxo-6-(3-trifluoromethylphenyl)-3,6-dihydro-2H-pyrimidine-1-carboxylic acid (2-hydroxy-ethyl)-amide Using 3-trifluoromethylbenzaldehyde and following a modification of the procedure described in Example 2, the title compound was obtained in 15% overall yield.

$^1$H-NMR (MeOH-d$_4$, 400 MHz): δ 7.63 (m, 1 H), 7.58 (m, 3 H), 6.25 (s, 1 H), 3.58 (m, 2 H), 3.35 (m, 2 H), 2.15 (s, 3 H). LC/MS (ES+) 369 (M+H)$^+$.

EXAMPLE 36

4 (3,5-Dichlorophenyl)-6-methyl-2-oxo-3-(thiophene-2-carbonyl)-1,2,3,4-tetrahydropyrimidine-5-carbonitrile Using 3,5-dichlorobenzaldehyde and following the procedure described in Example 2, the title compound was obtained in 5% overall yield.

$^1$H-NMR (DMSO-d$_6$, 400 MHz): δ 10.78 (s, 1 H), 7.96 (d, 1 H, J=4.8 Hz), 7.72 (d, 1 H, J=3.1 Hz), 7.64 (t, 1 H. J=1.8 Hz), 7.36 (d, 2 H, J=1.8 Hz), 7.17 (m, 1 H), 5.92 (s, 1 H), 2.82 (s, 3 H), 2.18 (s, 3 H). LC/MS (ES+) 415 (M+Na)$^+$.

EXAMPLE 37

5-Cyano-6-(3,5-difluorophenyl)-4-methyl-2-oxo-3,6-dihydro-2H-pyrimidine-1-carboxylic acid ethylamide Intermediate IX was obtained using 3,5-difluorobenzaldehyde and following the procedure described in Example 2. The title compound was obtained in 28% yield following the procedure of Example 3.

$^1$H-NMR (CD$_3$Cl, 400 MHz): δ 6.77 (m, 2 H), 6.67 (m, 1 H), 6.21 (s, 1 H), 3.27 (m, 2 H), 2.15 (s, 3 H), 1.12 (t, 3H, J=10.4 Hz). LC/MS (ES+) 321 (M+H)$^+$.

EXAMPLE 38

5-Cyano-6-(3,5-difluorophenyl)-4-methyl-2-oxo-3,6-dihydro-2H-pyrimidine-1-carboxylic acid ethyl ester Using 3,5-difluorobenzaldehyde and following the procedure described in Example 2, the tide compound was obtained in 36% yield for the final two steps.

$^1$H-NMR (CD3Cl, 400 MHz): δ 8.26 (s, 1 H), 6.83 (m, 2 H), 6.73 (m, 1 H), 5.80 (s, 1 H), 4.27 (m, 2 H), 2.15 (s, 3 H), 1.26 (t, 3H, J=10.4 Hz). LC/MS (ES+) 322 (M+H)$^+$.

EXAMPLE 39

4-(3,5-Difluorophenyl)-6-methyl-2-oxo-3-(piperidine-1-carbonyl)-1,2,3,4-tetrahydropyrimidine-5-carbonitrile Intermediate IX was obtained using 3,5-difluorobenzaldehyde and following the procedure described in Example 2. The title compound was obtained in 30% yield following the procedure of Example 3.

$^1$H-NMR (CD$_3$OD, 400 MHz): δ 7.01 (m, 3 H), 5.62 (s, 1 H), 5.48 (s, 1 H), 3.37 (m, 2 H), 3.24 (m, 2 H), 2.14 (s, 3 H), 1.84 (m, 4), 1.28 (m, 4H). LC/MS (ES+) 361 (M+H)$^+$.

EXAMPLE 40

4-(3,5-Difluorophenyl)-4-methyl-2-oxo-3-(pyrrolidine-1-carbonyl)-1,2,3,4-tetrahydropyrimidine-5-carbonitrile Intermediate IX was obtained using 3,5-difluorobenzaldehyde and following the procedure described in Example 2. The title compound was obtained in 18% yield following the procedure of Example 3.

$^1$H-NMR (CD$_3$OD, 400 MHz): δ 8.25 (s, 1 H), 8.24 (d, 1 H, J=7.9 Hz), 7.82 (d, 1 H, J=7.9 Hz), 7.67 (t, 2 H, J=7.9 Hz), 5.77 (s, 1H), 2.29–3.30 (m, 4 H), 2.16 (s, 3 H), 1.77 (m, 4). LC/MS (ES+) 355 (M+H)$^+$.

EXAMPLE 41

5-Cyano-4-methyl-6-naphthalene-1-yl-2-oxo-3,6-dihydro-2H-pyrimidine-1-carboxylic acid ethyl ester Using naphthalene-1-carboxaldehyde and following the procedure of Example 25, intermediate XXIV was obtained in 44% yield and the title compound was obtained in 22% yield.

¹H-NMR (DMSO-d₆, 400 MHz): δ 10.57 (s, 1 H), 8.40 (d, 1 H, J=8.4 Hz), 7.98 (d, 1 H, J=7.9 Hz), 7.94 (d, 1 H, J=8.4 Hz), 7.61 (m, 2 H), 7.55 (t, 1 H, J=7.0 Hz), 7.39 (d, 1 H, J=7.0 Hz), 6.73 (s, 1 H), 4.04 (m, 2 H), 2.05 (s, 3 H), 1.00 (t, 3 H, J=7.0 Hz). LC/MS (ES+) 336 (M+H)⁺.

EXAMPLE 42

5-Cyano-4-Methyl-6-naphthalene-1-yl-2-oxo-3,6-dihydro-2H-pyrimidine-1-carboxylic acid ethylamide Using naphthalene-1-carboxaldehyde and following the procedure of Example 25, intermediate XXIV was obtained in 44% yield. The title compound was obtained in 67% yield following the procedure described in Example 28.

¹H-NMR (CDCl₃, 400 MHz): δ 8.83 (t, 1 H, J=5.3 Hz), 8.43 (d, 1 H, J=8.4 Hz), 7.96 (s, 1 H), 7.84 (m, 2 H), 7.61 (m, 1 H), 7.52 (t, 1 H, J=7.0 Hz), 7.42 (t, 1 H, J=7.9 Hz), 7.36 (d, 1 H, J=6.2 Hz), 7.14 (s, 1 H), 3.30 (m, 1 H), 3.21 (m, 1 H), 1.92 (s, 3 H), 1.1 1 (t, 3 H, J=7.5 Hz). LC/MS (ES+) 335 (M+H)⁺, 357 (M+Na)⁺.

EXAMPLE 43

6-(3-Bromophenyl)-5-cyano-4-methyl-2-oxo-3,6-dihydro-2H-pyrimidine-1-carboxylic acid ethyl ester Using 3-bromobenzaldehyde and following the procedure of Example 25, intermediate XXIV was obtained in 25% yield and the title compound was obtained in 80% yield.

¹H-NMR (CDCl₃, 400 MHz): δ 7.48 (m, 2 H), 7.27 (m, 2 H), 5.87 (s, 1 H), 4.33 (m, 2 H), 2.22 (s, 3 H), 1.33 (t, 3 H, J=7.0 Hz). LC/MS (ES+) 364 (M+H)⁺.

EXAMPLE 44

6-(3-Bromophenyl)-5-cyano-4-methyl-2-oxo-3,6-dihydro-2H-pyrimidine-1-carboxylic acid ethylamide Using 3-bromobenzaldehyde and following the procedure of Example 25, intermediate XXIV was obtained in 25% yield. The title compound was obtained in 88% yield following the procedure described in Example 28.

¹H-NMR (CDCl₃, 400 MHz): δ 8.65 (t, 1 H, J=5.3 Hz), 7.91 (s, 1 H), 7.84 (m, 1 H), 7.38 (m, 1 H), 7.19 (m, 2 H), 6.24 (s, 1 H), 3.24 (m, 2 H), 2.10 (s, 3 H), 1.10 (t, 3 H, J=7.0 Hz). LC/MS (ES+) 363 (M+H)⁺.

EXAMPLE 45

5-Cyano-4-methyl-2-oxo-6-(2-trifluoromethylphenyl)-3,6-dihydro-2H-pyrimidine-1-carboxylic acid ethyl ester Using 2-trifluoromethylbenzaldehyde and following the procedure of Example 25, intermediate XXIV was obtained in 43% yield and the title compound was obtained in 30% yield.

¹H-NMR (DMSO-d₆, 400 MHz) δ 10.58 (s, 1 H), 7.77 (m, 2 H), 7.58 (t, 1 H. J=7.5 Hz), 7.51 (d, 1 H, J=8.4 Hz), 6.06 (d, 1 H, J=0.9 Hz), 4.06 (m, 2 H), 2.05 (d, 3 H, J=0.9 Hz), 1.05 (t, 3 H, J=7.0 Hz). LC/MS (ES+) 354 (M+H)⁺, 376 (M+Na)⁺.

EXAMPLE 46

5-Cyano-4-methyl-2-oxo-6-(2-trifluoromethylphenyl)-3,6-dihydro-2H-pyrimidine-1-carboxylic acid ethylamide Using 2-trifluoromethylbenzaldehyde and following the procedure of Example 25, intermediate XXIV was obtained in 43% yield. The title compound was obtained in 26% yield following the procedure described in Example 28.

¹H-NMR (MeOH-d₄, 400 MHz): δ 9.07 (s, 1 H), 7.69 (d, 1 H, J=7.9 Hz), 7.64 (d, 1 H, J=7.9 Hz), 7.54 (d, 1 H, J=7.9 Hz), 7.49 (t, 1 H, J=7.9 Hz), 6.48 (s, 1 H), 3.17 (m, 2 H), 2.11 (s, 3 H), 1.06 (t, 3 H, J=7.0 Hz). LC/MS (ES+) 353 (M+H)⁺, 375 (M+Na)⁺.

EXAMPLE 47

5-Cyano-6-(3-methoxycarbonylphenyl)-4-methyl-2-oxo-3,6-dihydro-2H-pyrimidine-1-carboxylic acid ethyl ester Using methyl 3-formylbenzoate and following the procedure of Example 25, intermediate XXIV was obtained in 30% yield and the title compound was obtained in 50% yield.

¹H-NMR (MeOH-d₄, 400 MHz): δ 8.02 (m, 2 H), 7.60 (m, 1 H), 7.52 (m, 1 H), 5.93 (s, 1 H), 4.28 (m, 2 H), 3.92 (s, 3 H), 2.18 (s, 3 H), 1.29 (t, 3 H, J=7.0 Hz). LC/MS (ES+) 344 (M+H)⁺, 366 (M+Na)⁺.

EXAMPLE 48

3-(5-Cyano-3-ethylcarbamoyl-6-methyl-2-oxo-1,2,3,4-tetrahydropyrimidin-4-yl)-benzoic acid methyl ester Using methyl 3-formylbenzoate and following the procedure of Example 25, intermediate XXIV was obtained in 30% yield. The title compound was obtained in 40% yield following the procedure described in Example 28.

¹H-NMR (MeOH-d₄, 400 MHz): δ 8.94 (s, 1 H), 7.89 (m, 2 H), 7.48 (d, 1 H, J=7.9 Hz), 7.40 (t, 1 H, J=7.9 Hz), 6.15 (s, 1 H), 3.83 (s, 3 H), 3.17 (m, 2 H), 2.07 (s, 3 H), 1.05 (t, 3 H, J=7.0 Hz). LC/MS (ES+) 343 (M+H)⁺, 365 (M+Na)⁺.

EXAMPLE 49

BMS-511181 6-Butyl-5-cyano-4-methyl-2-oxo-3,6-dihydro-2H-pyrimidine-1-carboxylic acid ethylamide Using 1-buteraldehyde and following the procedure of Example 26, intermediate XXIV was obtained in 97% yield. The title compound was obtained in 55% yield following the procedure described in Example 28.

¹H-NMR (DMSO-d₆, 400 MHz): δ 0.85 (t, 3 H, J=6.7), 1.07 (t, 3H, J=7.2), 1.23–1.29 (m, 4H), 1.44–1.60 (m, 2H), 2.05 (s, 3H), 3.17–3.32 (m, 2H), 5.04 (t, 1H, J=6.0), 8.70 (t, 1H, J=5.5), 10.30 (s, 1H). MS 263 (M–H)⁻.

EXAMPLE 50

6-(3,5-Bis-trifluoromethylphenyl)-5-cyano-4-methyl-2-oxo-3,6-dihydro-2H-pyrimidine-1-carboxylic acid ethylamide Using 3,5-bis-trifluoromethylbenzaldehyde and following the procedure of Example 25, intermediate XXIV was obtained in 100% yield. The title compound was obtained in 50% yield following the procedure described in Example 28.

¹H-NMR (CDCl₃, 400 MHz): δ 8.68 (t, 1 H, J=5.3 Hz), 7.86 (s, 1 H), 7.77 (s, 2 H), 7.48 (s, 1 H), 6.46 (s, 1 H), 3.31 (m, 2 H), 2.24 (s, 3 H), 1.17 (t, 3 H, J=7.0 Hz). LC/MS (ES+) 421 (M+H)⁺.

EXAMPLE 51

6-(2,5-Bis-trifluoromethylphenyl)-5-cyano-4-methyl-2-oxo-3,6-dihydro-2H-pyrimidine-1-carboxylic acid ethylamide Using 2,5-bis-trifluoromethlbenzaldehyde and following the procedure of Example 25, intermediate XXIV was obtained in 25% yield. The title compound was obtained in 38% yield following the procedure described in Example 28.

¹H-NMR (MeOH-d₄, 400 MHz): δ 7.94 (d, 1 H, J=8.4 Hz), 7.84 (d, 1 H, J=8.4 Hz), 7.75 (s, 1 H), 6.50 (s, 1 H), 3.17 (m, 2 H), 2.12 (d, 3 H, J=0.9 Hz), 1.05 (t, 3 H, J=7.0 Hz). LC/MS (ES+) 421 (M+H)⁺, 443 (M+Na)⁺.

EXAMPLE 52

6-(2,5-Bis-trifluoromethylphenyl)-5-cyano-4-methyl-2-oxo-3,6-dihydro-2H-pyrimidine-1-carboxylic acid ethyl ester Using 2,5-bis-trifluoromethlbenzaldehyde and following the procedure of Example 25, intermediate XXIV was obtained in 25% yield and the title compound was obtained in 55% yield.

¹H-NMR (CDCl₃, 400 MHz): δ 8.43 (s, 1 H), 7.88 (m, 1 H), 7.76 (m, 2 H), 6.25 (s, 1 H), 4.23 (q, 2 H, J=7.0 Hz), 2.22 (s, 3 H), 1.19 (t, 3 H, J=7.0 Hz). LC/MS (ES+) 422 (M+H)⁺.

EXAMPLE 53

5-Cyano-6-(3-ethylcarbamoylphenyl)-4-methyl-2-oxo-3,6-dihydro-2H-pyrimidine-1-carboxylic acid ethylamide Starting with the product of Example 48, the title compound was obtained in 57% yield by ester hydrolysis (lithium hydroxide in aqueous methanol) and coupling of the resulting carboxylic acid with ethylamine (water soluble carbodiimide and hydroxybenzotriazole in acetonitrile).

¹H-NMR (MeOH-d₄, 400 MHz): δ 8.97 (s, 1 H), 7.68 (d, 1 H, J=1.8 Hz), 7.65 (m, 1 H), 7.38 (m, 2 H), 6.10 (s, 1 H), 3.30 (m, 2 H), 3.13 (m, 2 H), 2.05 (s, 3 H), 1.12 (t, 3 H, J=7.0 Hz), 1.01 (t, 3 H, J=7.0 Hz). LC/MS (ES+) 356 (M+H)⁺.

EXAMPLE 54

5-Cyano-6-(3-cyano-4-fluorophenyl)-4-methyl-2-oxo-3,6-dihydro-2H-pyrimidine-1-carboxylic acid ethylamide Using 3-cyano-4-fluorobenzaldehyde and following the procedure of Example 25, intermediate XXIV was obtained in 62% yield. The title compound was obtained in 51% yield following the procedure described in Example 28.

¹H-NMR (CDCl₃, 500 MHz) δ 8.66 (s, 1 H), 7.74 (s, 1 H), 7.65 (m, 1 H), 7.57 (m, 1 H), 7.22 (t, 1 H, J=8.2 Hz), 6.32 (s, 1 H), 3.29 (m, 2 H), 2.22 (s, 3 H), 1.16 (t, 3 H, J=7.2 Hz). LC/MS (ES+) 328 (M+H)⁺, 350 (M+Na)⁺.

EXAMPLE 55

5-Cyano-6-(3-cyano 4-fluorophenyl)-4-methyl-2-oxo-3,6-dihydro-2H-pyrimidine-1-carboxylic acid ethyl ester Using 3-cyano-4-fluorobenzaldehyde and following the procedure of Example 25, intermediate XXIV was obtained in 62% yield and the title compound was obtained in 30% yield.

¹H-NMR (MeOH-d₄, 400 MHz): δ 7. 71 (m, 2 H), 7.38 (t, 1 H, J=(8.3 Hz), 5.93 (s, 1 H), 4.32 (m, 2 H), 2.20 (d, 3 H, J=0.9 Hz), 1.32 (d, 3 H, J=7.0 Hz). LC/MS (ES+) 329 (M+H)⁺.

EXAMPLE 56

5-Cyano-6-(2,2-dimethylpropyl)-4-methyl-2-oxo-3,6-dihydro-2H-pyrimidine-1-carboxylic acid ethylamide Using 2,2-dimethylpropionaldehyde and following the procedure of Example 26, intermediate XXIV was obtained in 57% yield. The title compound was obtained in 54% yield following the procedure described in Example 28.

¹H-NMR (DMSO-d₆, 400 MHz): δ 0.92 (s, 9H), 1.06 (t, 3H, J=7.15 Hz), 1.43–1.47 (m, 2H), 2.05 (s, 3H), 3.21 (m, 2H), 5.20 (m, 1H), 8.60 (m, 1H), 10.42 (s, 1H). MS 277 (M−H)⁻.

EXAMPLE 57

5-Cyano-6-cyclopropyl-4-methyl-2-oxo-3,6-dihydro-2H-pyrimidine-1-carboxylic acid ethyl ester Using cyclopropanecarboxaldehyde and following the procedure of Example 26, intermediate XXIV was obtained in 83% yield and the title compound was obtained in 36% yield.

¹H-NMR (DMSO-d₆, 400 MHz): δ 0.35–0.65 (m, 4H), 1.10–1.21 (m, 1H), 1.23 (t, 3H, J=7.09 Hz), 2.05 (s, 3H), 4.18–4.21 (m, 2 H), 4.33 (d, 1H, J=8.13 Hz), 10.36 (s, 1H). MS 248 (M−H)⁻.

EXAMPLE 58

5-Cyano-6-cyclopropyl-4-methyl-2-oxo-3,6-dihydro-2H-pyrimidine-1-carboxylic acid ethylamide Using cyclopropanecarboxaldehyde and following the procedure of Example 26, intermediate XXIV was obtained in 83% yield. The title compound was obtained in 15% yield following the procedure described in Example 28.

¹H-NMR (DMSO-d₆, 400 MHz): δ 0.36–0.51 (m, 4H), 1.05–1.09 (m, 4H), 2.06 (s, 3H), 3.20–3.23 (m, 2 H), 4.66 (d, 1H, J=8.30 Hz), 8.74 (m, 1H), 10.36 (s, 1H). MS 247 (M−H)⁻. HRMS 247.1195 (M−H)⁻.

EXAMPLE 59

5-Cyano-6-(2-fluoro-5-trifluoromethylphenyl)-4-methyl-2-oxo-3,6-dihydro-2H-pyrimidine-1-carboxylic acid ethylamide Using 2-fluoro-5-trifluoromethylbenzaldehyde and following the procedure of Example 25, intermediate XXIV was obtained in 41% yield. The title compound was obtained in 75% yield following the procedure described in Example 28.

¹H-NMR (CDCl₃, 400 MHz): δ 8.68 (t, 1 H, J=4.8 Hz), 7.60 (m, 2 H), 7.37 (s, 1 H), 7.22 (t, 1 H, J=9.2 Hz), 6.41 (s, 1 H), 3.30 (m, 1 H), 3.24 (m, 1 H), 2.18 (d, 3 H, J=0.9 Hz), 1.14 (t, 3 H, J=7.0 Hz). LC/MS (ES+) 371 (M+H)⁺, 393 (M+Na)⁺.

EXAMPLE 60

5-Cyano-6-(2-fluoro-5-trifluoromethylphenyl)-4-methyl-2-oxo-3,6-dihydro-2H-pyrimidine-1-carboxylic acid ethyl ester Using 2-fluoro-5-trifluoromethylbenzaldehyde and following the procedure of Example 25, intermediate XXIV was obtained in 41% yield and the title compound was obtained in 38% yield.

¹H-NMR (CDCl₃, 400 MHz): δ 8.27 (s, 1 H), 7.65 (m, 1 H), 7.58 (m, 1 H), 7.25 (t, 1 H, J=9.2 Hz), 6.03 (s, 1 H), 4.28 (m, 2 H), 2.20 (d, 3 H, J=0.9 Hz), 1.29 (t, 3 H, J=7.0 Hz). LC/MS (ES+) 372 (M+H)⁺, 394 (M+Na)⁺.

EXAMPLE 61

5-Cyano-6-isopropyl-4-methyl-2-oxo-3,6-dihydro-2H-pyrimidine-1-carboxylic acid ethyl ester Using cyclopropanecarboxaldehyde and following the procedure of Example 26, intermediate XXIV was obtained in 76% yield and the title compound was obtained in 23% yield.

¹H-NMR (DMSO-d₆, 400 MHz): δ 0.88–0.92 (m, 6H), 1.23 (t, 3H, J=7.10 Hz), 1.90–1.95 (m, 1H), 2.07 (s, 3H), 4.16–4.22 (m, 2H), 4.51 (d, 1H, J=6.82 Hz), 10.37 (s, 1H). MS: 250 (M–H)⁻.

EXAMPLE 62

5-Cyano-4-methyl-6-naphthalene-2-yl-2-oxo-3,6-dihydro-2H-pyrimidine-1-carboxylic acid ethyl ester Using naphthalene-2-carboxaldehyde and following the procedure of Example 25, intermediate XXIV was obtained in 64% yield and the title compound was obtained in 39% yield.

¹H-NMR (DMSO-d₆, 400 MHz): δ 10.54 (s, 1 H), 7.96 (m, 3 H), 7.78 (s, 1 H), 7.56 (m, 2 H), 7.44 (d, 1 H, J=8.3 Hz), 5.98 (s, 1 H), 4.18 (q, 2 H, J=7.0 Hz), 2.12 (s, 3 H), 1.20 (t, 3 H, J=7.0 Hz). LC/MS (ES+) 336 (M+H)⁺.

EXAMPLE 63

5-Cyano-6-[3-(2-hydroxyethylcarbamoyl)-phenyl]-4-methyl-2-oxo-3,6-dihydro-2H-pyrimidine-1-carboxylic acid ethylamide Starting with the product of Example 48, the title compound was obtained in 60% yield by ester hydrolysis (lithium hydroxide in aqueous methanol) and coupling of the resulting carboxylic acid with 2-aminoethanol (water soluble carbodiimide and hydroxybenzotriazole in acetonitrile).

¹H-NMR (CDCl₃, 400 MHz): δ 8.73 (t, 1 H, J=5.3 Hz), 8.03 (s, 1 H), 7.75 (t, 1 H, J=1.8 Hz), 7.68 (m, 1 H), 7.51 (d, 1 H, J=7.5 Hz), 7.39 (t, 1 H, J=7.5 Hz), 7.00 (t, 1 H, J=4.8 Hz), 6.29 (s, 1 H), 3.80 (t, 2 H, J=4.8 Hz), 3.59 (q, 2 H, J=4.8 Hz), 3.31 (m, 1 H), 3.22 (m, 1 H), 2.18 (s, 3 H), 1.13 (t, 3 H, J=7.0 Hz). LC/MS (ES+) 372 (M+H)⁺, 394 (M+Na)⁺.

EXAMPLE 64

5-Cyano-6-(2-methoxyphenyl)-4-methyl-2-oxo-3,6-dihydro-2H-pyrimidine-1-carboxylic acid ethyl ester Using 2-methoxybenzaldehyde and following the procedure of Example 26, intermediate XXIV was obtained in 17% yield and the tide compound was obtained in 28% yield.

¹H-NMR (400 MHz, CDCl₃): δ 1.27 (t, J=7.0 Hz, 3H), 2.12 (d, J=0.6 Hz, 3H), 3.86 (s, 3H), 4.25 (m, 2H), 6.04 (s, 1H), 6.93 (m, 2H), 7.06 (s, 1H), 7.2 (m, 1H), 7.33 (m, 1H). MS 316 (M+H)⁺.

EXAMPLE 65

5-Cyano-6-(2-methoxyphenyl)-4-methyl-2-oxo-3,6-dihydro-2H-pyrimidine-1-carboxylic acid ethylamide Using 2-methoxybenzaldehyde and following the procedure of Example 26, intermediate XXIV was obtained in 17% yield. Using the procedure of Example 27, the title compound was obtained in 8% yield.

¹H-NMR (400 MHz, CDCl₃): δ 1.13 (t, J=7.0 Hz, 3H), 2.1 (s, 3H), 3.25 (m, 1H), 3.33 (m, 1 H), 3.86 (s, 3H), 6.47 (s, 1H), 6.62 (s, 1H), 6.9 (m, 2H), 7.2 (dd, J1=1.5 Hz, J2=7.6 Hz, 1H), 7.3 (dt, J1=1.7 Hz, J2=7.2 Hz, 1H), 8.7 (bs, 1H). MS 315 (M+H)⁺.

EXAMPLE 66

6-(2-Allyloxyphenyl)-5-cyano-4-methyl-2-oxo-3,6-dihydro-2H-pyrimidine-1-carboxylic acid ethyl ester Using 2-allyloxybenzaldehyde and following the procedure of Example 26, intermediate XXIV was obtained in 33% yield and the title compound was obtained in 43% yield.

¹H-NMR (400 MHz, CDCl₃): δ 1.26 (t, J=7.0 Hz, 3H), 2.1 (s, 3H), 4.25 (m, 2H), 4.6 (m, 2H), 5.30 (d, J=10.4 Hz, 1H), 5.36 (d, J=16.0 Hz), 6.0 (s, 1H), 6.1 (m, 1H), 6.9 (m, 3H), 7.25 (m, 2H). MS 342 (M+H)⁺.

EXAMPLE 67

6-(2-Allyloxyphenyl)-5-cyano-4-methyl-2-oxo-3,6-dihydro-2H-pyrimidine-1-carboxylic acid ethylamide Using 2-allyloxybenzaldehyde and following the procedure of Example 26, intermediate XXIV was obtained in 33% yield. Using the procedure of Example 27, the title compound was obtained in 23% yield.

¹H-NMR (400 MHz, CDCl₃): δ 1.12 (t, J=7.0 Hz, 3H), 2.1 (s, 3H), 3.2 (m, 1H), 3.3 (m, 1H), 4.6 (m, 2H), 5.35 (m, 2H), 6.1 (m, 1H), 6.38 (s, 1H), 6.50 (s, 1H), 6.9 (m, 2H), 7.25 (m, 2H), 8.7 (bs, 1H). MS 341 (M+H)⁺.

EXAMPLE 68

6-(2-Bromophenyl)-5-cyano-4-methyl-2-oxo-3,6-dihydro-2H-pyrimidine-1-carboxylic acid ethyl ester Using 2-bromobenzaldehyde and following the procedure of Example 25, intermediate XXIV was obtained in 50% yield and the title compound was obtained in 31% yield.

¹H-NMR (400 MHz, CDCl₃): δ 1.24 (t, J=7.2 Hz, 3H), 2.16 (s, 3H), 4.24 (q, J=7.1 Hz, 2H), 6.33 (s, 1H), 7.20 (m, 1H), 7.33 (m, 3H), 7.6 (d, J=8.0 Hz, 1H). MS 364 (M+H)⁺.

EXAMPLE 69

6-(2-Bromophenyl)-5-cyano-4-methyl-2-oxo-3,6-dihydro-2H-pyrimidine-1-carboxylic acid ethylamide Using 2-bromobenzaldehyde and following the procedure of Example 25, intermediate XXIV was obtained in 50% yield. The title compound was obtained in 46% yield following the procedure described in Example 28.

¹H-NMR (MeOH-d₄, 500 MHz): δ 7.55 (m, 1 H), 7.30 (m, 2 H), 7.15 (m, 1 H), 6.46 (s, 1 H), 3.14 (m, 2 H), 2.04 (s, 3 H), 1.04 (t, 3 H, J=7.1 Hz). LC/MS (ES+) 364 (M+H⁺).

EXAMPLE 70

5-Cyano-6-(3-methoxyphenyl)-4-methyl-2-oxo-3,6-dihydro-2H-pyrimidine-1-carboxylic acid ethylamide Using 3-methoxybenzaldehyde and following the procedure of Example 25, intermediate XXIV was obtained in 66% yield. The title compound was obtained in 62% yield following the procedure described in Example 28.

¹H-NMR (DMSO-d₆, 500 MHz): δ 10.49 (s, 1 H), 8.79 (t, 1 H, J=5.5 Hz), 7.32 (t, 1 H, J=7.7 Hz), 6.92 (m, 1 H), 6.81 (d, 1 H, J=7.7 Hz), 6.75 (s, 1 H), 6.06 (s, 1 H), 3.74 (s, 3 H), 3.17 (m, 2 H), 2.07 (s, 3 H), 1.04 (t, 3 H, 1=7.1 Hz). LC/MS (ES+) 315 (M+H⁺).

EXAMPLE 71

6-(2-Benzyloxyphenyl)-5-cyano-4-methyl-2-oxo-3,6-dihydro-2H-pyrimidine-1-carboxylic acid ethyl ester Using 2-benzyloxybenzaldehyde and following the procedure of Example 26, intermediate XXIV was obtained in 47% yield and the title compound was obtained in 54% yield.

¹H-NMR (CDCl₃, 400 MHz): δ 1.25 (t, J=7.0 Hz, 3H), 1.82 (d, J=0.9 Hz, 3H), 4.21 (m, 2H), 5.04 (dd, J1=10.5 Hz, J2=31.2 Hz, 2H), 5.71 (s, 1H), 5.84 (s, 1H), 6.96 (m, 2H), 7.30 (m, 2H), 7.45 (m, 5H). MS 392 (M+H)⁺.

EXAMPLE 72

6-Benzyloxymethyl-5-cyano-4-methyl-2-oxo-3,6-dihydro-2H-pyrimidine-1-carboxylic acid ethylamide Using 2-benzyloxyacetaldehyde and following the procedure of Example 26, intermediate XXIV was obtained in 45% yield. The title compound was obtained in 30% yield following the procedure described in Example 28.

¹H-NMR (DMSO-d₆): δ 1.10 (t, 3H, J=7.33 Hz), 2.07 (s, 3H), 3.22–3.26 (m, 2H), 3.49–3.52 (m, 2H), 4.51 (s, 2H), 5.29 (m, 1H), 7.27–7.34 (m, 5H), 7.90 (br m, 1H), 8.75 (br m, 1H). MS: 327 (M–H)⁻. HRMS 327.1450 (M–H)⁻.

EXAMPLE 73

6-Benzyloxymethyl-5-cyano-4-methyl-2-oxo-3,6-dihydro-2H-pyrimidine-1-carboxylic acid ethyl ester Using 2-benzyloxyacetaldehyde and following the procedure of Example 26, intermediate XXIV was obtained in 45% yield and the title compound was obtained in 80% yield.

¹H-NMR (DMSO-d6): δ 1.28 (t, 3H, J=7.13), 2.05 (s, 3H), 3.58–3.70 (m, 2H), 4.29–4.35 (m, 2H), 4.53 (s, 3H), 4.97-4.99 (m, 1H), 7.25–7.35 (m, 5H). MS: 328 (M–H)⁻. 328.1297 HRMS (M–H)⁻.

EXAMPLE 74

6-Bromo-4-fluorophenyl)-5-cyano-4-methyl-2-oxo-3,6-dihydro-2H-pyrimidine-1-carboxylic acid ethylamide Using 3-bromo-4-fluorobenzaldehyde and following the procedure of Example 26, intermediate XXIV was obtained in 99% yield. The title compound was obtained in 69% yield following the procedure described in Example 28.

¹H-NMR (DMSO-d₆, 400 MHz): δ 10.55 (s, 1 H), 8.75 (t, 1 H, J=5.3 Hz), 7.55 (m, 1 H), 7.42 (t, 1 H, J=8.8 Hz), 7.33 (m, 1 H), 6.10 (s, 1 H), 3.16 (m, 2 H), 2.09 (s, 3 H), 1.03 (t, 3 H, J=7.0 Hz). LC/MS (ES+) 381 (M+H⁺).

EXAMPLE 75

6-(3-Bromo-4-fluorophenyl)-5-cyano-4-methyl-2-oxo-3,6-dihydro-2H-pyrimidine-1-carboxylic acid cyclopropylamide Using 3-bromo-4-fluorobenzaldehyde and following the procedure of Example 26, intermediate XXIV was obtained in 99% yield. The title compound was obtained in 54% yield following the procedure described in Example 28.

¹H-NMR (MeOH-d₄, 500 MHz): δ 57.46 (m, 1 H), 7.25 (m, 1 H), 7.14 (t, 1 H, J=8.8 Hz), 6.04 (s, 1 H), 2.54 (m, 1 H), 2.05 (s, 3 H), 0.63 (m, 2 H), 0.42 (m, 1 H), 0.37 (m, 1 H). LC/MS (ES+) 393 (M+H⁺).

EXAMPLE 76

6-(5-Bromo-2-fluorophenyl)-5-cyano-4-methyl-2-oxo-3,6-dihydro-2H-pyrimidine-1-carboxylic acid ethylamide Using 5-bromo-2-fluorobenzaldehyde and following the procedure of Example 26, intermediate XXIV was obtained in 71% yield. The title compound was obtained in 70% yield following the procedure described in Example 28.

¹H-NMR (MeOH-d₄, 500 MHz): δ 7.50 (m, 1 H), 7.43 (m, 1 H), 7.10 (m, 1 H), 6.22 (s, 1 H), 3.22 (m, 2H), 2.11 (d, 3H, J=2.2 Hz), 1.11 (m, 3 H).

EXAMPLE 77

6-Bromo-2-fluorophenyl)-5-cyano-4-methyl-2-oxo-3,6-dihydro-2H-pyrimidine-1-carboxylic acid cyclopropylamide Using 5-bromo-2-fluorobenzaldehyde and following the procedure of Example 26, intermediate XXIV was obtained in 71% yield. The title compound was obtained in 70% yield following the procedure described in Example 28.

¹H-NMR (MeOH-d₄, 500 MHz): δ 7.51 (m, 1 H), 7.44 (m, 1 H), 7.11 (m, 1 H), 6.21 (s, 1 H), 2.60 (m, 1 H), 2.10 (d, 3 H, J=1.6 Hz), 0.70 (m, 2 H), 0.51 (m, 1 H), 0.44 (m, 1 H).

EXAMPLE 78

5-Cyano-6-(3,5-dibromophenyl)-4-methyl-2-oxo-3,6-dihydro-2H-pyrimidine-1-carboxylic acid ethylamide Using 3,5-dibromobenzaldehyde and following the procedure of Example 26, intermediate XXIV was obtained in 46% yield. The title compound was obtained in 83% yield following the procedure described in Example 28.

¹H-NMR (DMSO-d₆, 400 MHz) δ 10 60 (br s, 1 H); 8.77 (t, J=5.4 Hz, 1 H); 7.85 (t, J=1.6 Hz, 1 H); 7.42 (d, J=1.7 Hz, 2 H); 6.08 (s, 1 H); 3.18–3.26 (m, 2 H); 2.08 (s, 3 H), 1.03 (t, J=7.1 Hz, 3 H). LC/MS (ES+) 441 (M+H)⁺.

EXAMPLE 79

5-Cyano-4-methyl-6-(3-nitrophenyl)-2-oxo-3,6-dihydro-2H-pyrimidine-1-carboxylic acid cyclopropytmethylamide Using 3-nitrobenzaldehyde and following the procedure of Example 26, intermediate XXIV was obtained in 92% yield. The title compound was obtained in 53% yield following the procedure described in Example 28.

¹H-NMR (MeOH-d₄, 500 MHz): δ 9.15 (s, 1 H), 8.21 (m, 1 H), 8.17 (d, 1 H, J=1.6 Hz), 7.76 (d, 1 H, J=7.7 Hz), 7.66 (t, 1 H, J=7.7 Hz), 6.29 (s, 1 H), 3.68 (d, 1 H, J=7.1 Hz), 3.09 (m, 2 H), 2.17 (s, 3 H), 0.98 (m, 1 H), 0.48 (m, 2 H), 0.20 (m, 2 H). LC/MS (ES+) 356 (M+H⁺).

EXAMPLE 80

5-Cyano-4-methyl-2-oxo-6-phenethyloxymethyl-3,6-dihydro-2H-pyrimidine-1-carboxylic acid ethyl ester Using 2-phenethyloxyacetaldehyde and following the procedure of Example 26, intermediate XXIV was obtained in 38% yield and the title compound was obtained in 18% yield.

¹H-NMR (DMSO-d₆, 400 MHz): 1.23 (t, 3H, J=7.1 Hz), 2.00 (s, 3H), 2.75 (t, 2H, J=6.7 Hz), 3.59–3.85 (m, 4H), 4.18–4.20 (m, 2H), 4.81 (br m, 1H), 7.19–7.27 (m, 5H), 10.26 (s, 1H). MS 342 (M–H)⁻. HRMS 342.1458 (M–H)⁻.

EXAMPLE 81

5-Cyano-4-methyl-2-oxo-6-phenethyl-3,6-dihydro-2H-pyrimidine-1-carboxylic acid ethylamide Using 3-phenylpropionaldehyde and following the procedure of Example 26, intermediate XXIV was obtained in 58% yield. The title compound was obtained in 42% yield following the procedure described in Example 28.

$^1$H-NMR (DMSO$_6$, 400 MHz): 1.07 (t, 3H, J=7.1 Hz), 1.80–2.03 (m, 2H), 2.06 (s, 3H), 2.51–2.75 (m, 2H), 3.19–3.22 (m, 2H), 5.12 (br m, 1H), 7.18–7.30 (m, 5H), 8.70 (br m, 1H), 10.36 (s, 1H). MS 311 (M–H)$^-$. HRMS 311.1493 (M–H)$^-$.

EXAMPLE 82

5-Cyano-4-methyl-2-oxo-6-thiophen-3-yl-3,6-dihydro-2H-pyrimidine-1-carboxylic acid ethyl ester Using thiophene-3-carboxaldehyde and following the procedure of Example 26, intermediate XXIV was obtained in 50% yield and the title compound was obtained in 30% yield.

$^1$H-NMR (DMSO-d$_6$, 400 MHz): δ 1.23 (t, J=7.1 Hz, 3H), 2.10 (s, 3H), 4.21 (m, 2H), 5.87 (s, 1H), 7.03 (m, 1H), 7.44 (s, 1H), 7.60 (m, 1H), 10.48 (s, 1H). MS 292 (ES+): 292 (M+H)$^+$.

EXAMPLE 83

5-Cyano-4-methyl-6-(5-methylisoxazol-3-yl)-2-oxo-3,6-dihydro-2H-pyrimidine-1-carboxylic acid ethyl ester Using 5-methylisoxazole-3-carboxaldehyde and following the procedure of Example 26, intermediate XXIV was obtained in 27% yield and the title compound was obtained in 67% yield.

$^1$H-NMR (DMSO-d$_6$, 400 MHz): δ 10.52 (s, 1H), 6.20 (s, 1H), 5.95 (s, 1H), 4.21 (q, 2H, J=7.0 Hz), 2.40 (s, 3H), 2.05 (s, 3H), 1.22 (t, 3H, J=7.0 Hz). $^{13}$C-NMR (DMSO-d$_6$, 400 MHz): δ 170.87, 161.63, 151.86, 150.57, 147.09, 116.44, 99.35, 81.29, 63.08, 49.55, 16.85, 13.68, 11.56. MS (ESI), 291 (M+H)$^+$.

EXAMPLE 84

5-Cyano-6-(3,5-dimethylisoxazol-4-yl)-4-methyl-2-oxo-3,6-dihydro-2H-pyrimidine-1-carboxylic acid ethyl ester Using 3,5-dimethylisoxazole-4-carboxaldehyde and following the procedure of Example 26, intermediate XXIV was obtained in 74% yield and the title compound was obtained in 47% yield.

$^1$H-NMR (DMSO-d$_6$, 400 MHz): δ 10.56 (s, 1 H), 5.82 (s, 1H), 4.15 (q, 2H, J=7.0 Hz), 2.38 (s, 3H), 2.14 (s, 1H), 2.07 (s, 3H), 1.17 (t, 3H, J=7.0 Hz). $^{13}$C-NMR (DMSO-d$_6$, 400 MHz): δ 167.03, 157.45, 152.17, 147.60, 146.95, 116.44, 113.45, 81.58, 62.96, 48.58, 16.77, 13.64, 10.50, 9.57. MS (ESI), 305 (M+H)$^+$.

EXAMPLE 85

5-Cyano-4-methyl-2-oxo-6-thiophen-2-yl-3,6-dihydro-2H-pyrimidine-1-carboxylic acid ethyl ester Using thiophene-2-carboxaldehyde and following the procedure of Example 26, intermediate XXIV was obtained in 41% yield and the title compound was obtained in 58% yield.

$^1$H-NMR (DMSO-d$_6$, 400 MHz): δ 1.25 (t, J=7.1 Hz, 3H), 2.12 (s, 3H), 4.24 (m, 2H), 6.08 (s, 1H), 7.02 (m, 1H), 7.07 (d, J=3.4 Hz, 1H), 7.56 (m, 1H), 10.58 (s, 1H). MS (ESI) 290 (M–H)$^-$. HRMS (ESI) 290.0598 (M–H)$^-$.

EXAMPLE 86

5-Cyano-4-methyl-6-(3-methylthiophen-2-yl)-2-oxo-3,6-dihydro-2H-pyrimidine-1-carboxylic acid ethylamide Using 3-methylthiophene-2-carboxaldehyde and following the procedure of Example 26, intermediate XXIV was obtained in 33% yield. The title compound was obtained in 17% yield following the procedure described in Example 28.

$^1$H NMR (DMSO-d$_6$, 400 MHz): δ 1.03 (t, J=7.2 Hz, 3H), 2.05 (s, 3H), 3.15 (m, 2H), 3.33 (s, 3H), 6.41 (s, 1H), 6.82 (d, J=5.1 Hz, 1H), 7.35 (d, J=5.1 Hz, 1H), 8.73 (t, J=5.6 Hz, 1H), 10.62 (s, 1H). MS (ESI) 303 (M–H)$^-$. HRMS (ESI) 303.0927 (M–H)$^-$.

EXAMPLE 87

5-Cyano-4-methyl-6-(3-methylthiophen-2-yl)-2-oxo-3,6-dihydro-2H-pyrimidine-1-carboxylic acid ethyl ester Using 3-methylthiophene-2-carboxaldehyde and following the procedure of Example 26, intermediate XXIV was obtained in 33% yield and the title compound was obtained in 14% yield.

$^1$H-NMR (DMSO-d$_6$, 400 MHz): δ 1.20 (t, J=7.1 Hz, 3H), 2.05 (s, 3H), 3.33 (s, 3H), 4.17 (q, J=7.1 Hz, 2H), 6.14 (s, 1H), 6.84 (d, J=5.1 Hz, 1H), 7.38 (d, J=5.1 Hz, 1H), 10.61 (s, 1H). MS (ESI) 304 (M–H). HRMS (ESI) 304.0746 (M–H)$^-$.

EXAMPLE 88

5-Cyano-4-methyl-6-(2-methylthiazol-4-yl)-2-oxo-3,6-dihydro-2H-pyrimidine-1-carboxylic acid ethyl ester Using 2-methylthiazole-4-carboxaldehyde and following the procedure of Example 26, intermediate XXIV was obtained in 26% yield and the title compound was obtained in 16% yield.

$^1$H-NMR (CDCl$_3$, 400 MHz): δ 7.96 (s, 1H), 7.1 1 (s, 1H), 5.93 (s, 1H), 4.31 (m, 2H), 2.67 (s, 3H), 2.16 (s, 3H), 1.32 (t, 3H, J=6.9 Hz); $^{13}$C-NMR (CDCl$_3$, 400 MHz): δ 168.13, 152.34, 151.77, 149.06, 147.71, 116.31, 115.88, 85.39, 64.24, 35.87, 19.17, 17.81, 14.09. MS (ESI) 307 (M+H)$^+$.

EXAMPLE 89

6-(4-Bromothiophen-2-yl)-5-cyano-4-methyl-2-oxo-3,6-dihydro-2H-pyrimidine-1-carboxylic acid ethylamide Using 4-bromothiophene-2-carboxaldehyde and following the procedure of Example 26, intermediate XXIV was obtained in 68% yield. The title compound was obtained in 49% yield following the procedure described in Example 28.

$^1$H-NMR (DMSO-d$_6$, 400 MHz): δ 1.07 (t, J=7.1 Hz, 3H), 2.15 (s, 3H), 3.22 (m, 2H), 6.36 (s, 1H), 7.06 (s, 1H), 7.67 (s, 1H), 8.68 (t, J=5.6 Hz, 1H), 10.64 (s, 1H). MS (ES+) 369 (M+H)$^+$. HRMS (ESI): 366.9876 (M–H)$^-$.

EXAMPLE 90

6-(4-Bromothiophen-2-yl)-5-cyano-4-methyl-2-oxo-3,6-dihydro-2H-pyrimidine-1-carboxylic acid ethyl ester Using 4-bromothiazole-2-carboxaldehyde and following the procedure of Example 26, intermediate XXIV was obtained in 68% yield and the title compound was obtained in 45% yield. $^1$H-NMR (DMSO-d$_6$, 400 MHz): δ 1.25 (t, J=7.1 Hz, 3H), 2.14 (s, 3H), 4.24 (m, 2H), 6.09 (s, 1H), 7.10 (s, 1H), 7.71 (s, 1H), 10.63 (s, 1H). MS (ESI) 368 [M–H]$^-$. HRMS (ESI) 367.9697 (M–H)$^-$.

EXAMPLE 91

5-Cyano-4-methyl-2-oxo-6-[2-(4-trifluoromethylphenyl)-thiazol-4-yl]-3,6-dihydro-2H-pyrimidine-1-carboxylic acid ethyl ester Using 2-(4-trifluoromethylphenyl)thiazole-4-carboxaldehyde and following the procedure of Example 26, intermediate XXIV was obtained in 17% yield and the title compound was obtained in 31% yield.

$^1$H-NMR (DMSO-d$_{6, 400}$ MHz): δ 10.53 (s, 1H), 8.08 (d, 2H, J=8.2 Hz), 7.89 (d, 2H, J=8.1 Hz), 7.78 (s, 1H), 5.96 (s, 1H), 4.20 (m, 2H), 2.07 (s, 3H), 1.22 (t, 3H, J=7.1 Hz); $^{13}$C-NMR (DMSO-D$_6$, 400 MHz): δ 166.18, 154.51, 152.00, 149.60, 142.48, 135.79, 130.05, 129.78, 126.45, 125.96, 124.71, 122.30, 117.75, 116.84, 82.69, 62.83, 52.82, 16.87, 13.66. MS (ESI), 437 (M+H)$^+$.

EXAMPLE 92

6-[5-(4-Chlorophenyl)-oxazol-4-yl]-5-cyano-4-methyl-2-oxo-3,6-dihydro-2H-pyrimidine-1-carboxylic acid ethyl ester Using 5-(4-Chlorophenyl)oxazole-4-carboxaldehyde and following the procedure of Example 26, intermediate XXIV was obtained in 22% yield and the title compound was obtained in 16% yield.

$^1$H-NMR (DMSO-d$_6$, 400 MHz): δ 10.48 (s, 1H), 8.47 (m, 1H), 7.79 (d, 2H, J=8.6 Hz), 7.64 (d, 2H, J=8.6 Hz), 6.14 (s, 1H), 4.01 (q, 2H, J=7.1 Hz), 2.05 (s, 3H), 0.96 (t, 3H, J=7.1 Hz); $^{13}$C-NMR (DMSO-D$_6$, 400 MHz): δ 152.07, 151.98, 149.50, 147.60, 143.20, 133.40, 133.20129.01, 127.58, 125.33, 116.82, 81.25, 62.71, 49.80, 16.80, 13.20. MS (ESI), 387 (M+H)$^+$.

EXAMPLE 93

6-(2-Bromothiazol-5-yl)-5-cyano-4-methyl-1-oxo-3,6-dihydro-2H-pyrimidine-1-carboxylic acid ethyl ester Using 2-Bromothiazole-5-carboxaldehyde and following the procedure of Example 26, intermediate XXIV was obtained in 44% yield and the title compound was obtained in 41% yield.

$^1$H-NMR (DMSO-d$_6$, 400 MHz): δ 10.67 (s, 1H), 7.72 (s, 1H), 6.15 (s, 1H), 4.26 (m, 2H), 2.15 (s, 3H), 1.27 (t, 3H, J=7.1 Hz); $^{13}$C-NMR (DMSO-D$_6$, 400 MHz): δ 152.49, 151.78, 147.11, 141.99, 140.14, 137.93, 116.70, 82.49, 63.91, 50.06, 17.52, 14.18. MS (ESI), 371.0 (M+H)$^+$.

EXAMPLE 94

5-Cyano-4-methyl-2-oxo-6-(4-phenylthiophen-2-yl)-3,6-dihydro-2H-pyrimidine-1-carboxylic acid ethylamide Using 4-bromothiophene-2-carboxaldehyde and following the procedure of Example 26, intermediate XXIV was obtained in 68% yield. The 4-bromothienyl intermediate was converted to 4-phenylthienyl intermediate by the Suzuki reaction in 91% yield The title compound was obtained in 33% yield following the procedure described in Example 28.

$^1$H-NMR (DMSO-d$_{6, 400}$ MHz): δ 1.07 (t, J=7.1 Hz, 3H), 2.17 (s, 3H), 3.23 (m, 2H), 6.42 (s, 1H), 7.30 (t, J=5.1 Hz, 1H), 7.41–7.43 (m, 3H), 7.66–7.68 (m, 2H), 7.83 (s, 1H), 8.71 (t, J=5.6 Hz, 1H), 10.61 (s, 1H). MS (ESI) 365 (M–H)$^-$. HRMS (ESI) 365.1064 (M–H)$^-$.

EXAMPLE 95

6-[5-(4-Chlorophenyl)-furan-2-yl]-5-cyano-4-methyl-2-oxo-3,6-dihydro-2H-pyrimidine-1-carboxylic acid ethylamide Using 5-(4-Chlorophenyl)furan-2-carboxaldehyde and following the procedure of Example 26, intermediate XXIV was obtained in 16% yield. The title compound was obtained in 43% yield following the procedure described in Example 28.

$^1$H-NMR (DMSO-d$_6$, 400 MHz): δ 1.07 (t, J=7.1 Hz, 3H), 2.12 (s, 3H), 3.22 (m, 2H), 6.27 (s, 1H), 6.46 (d, J=3.4 Hz, 1H), 6.97 (d, J=3.4 Hz, 1H), 7.51 (m, 2H), 7.63 (m, 2H), 8.70 (t, J=5.5 Hz, 1H), 10.62 (s, 1H). MS (ESI) 383 (M–H)$^-$. HRMS (ESI) 383.0913 (M–H)$^-$.

EXAMPLE 96

5-Cyano-4-methyl-2-oxo-6-(4-trifluoromethylthiazol-5-yl)-3,6-dihydro-2H-pyrimidine-1-carboxylic acid ethyl ester Using 4-trifluoromethylthiazole-5-carboxaldehyde and following the procedure of Example 26, intermediate XXIV was obtained in 63% yield and the title compound was obtained in 52% yield.

$^1$H-NMR (DMSO-d$_6$, 400 MHz): δ 10.84 (s, 1H), 9.22 (s, 1H), 6.45 (s, 1H), 4.15 (q, 2H, J=5.7 Hz), 2.06 (s, 3H), 1.16 (t, 3H, J=5.7 Hz). $^{13}$C-NMR (DMSO-D$_6$, 400 MHz): δ 165.51, 151.90, 149.88, 146.79, 142.70, 138.70, 116.10, 83.68, 63.78, 50.42, 17.44, 13.94; MS (ESI) 361 (M+H)$^+$.

EXAMPLE 97

5-Cyano-4-methyl-2-oxo-6-(4-trifluoromethylthiazol-5-yl)-3,6-dihydro-2H-pyrimidine-1-carboxylic acid ethylamide Using 4-trifluoromethylthiazole-5-carboxaldehyde and following the procedure of Example 26, intermediate XXIV was obtained in 63% yield. The title compound was obtained in 59% yield following the procedure described in Example 28.

$^1$H-NMR (DMSO-d$_6$, 400 MHz): δ 10.84 (s, 1H), 9.19 (s, 1H), 8.69 (m, 1H), 6.68 (s, 1H), 3.15 (m, 1H), 2.06 (s, 3H), 1.01 (t, 3H, J=7.0 Hz); $^{13}$C-NMR (DMSO-d$_6$, 400 MHz): δ 155.54, 151.46, 150.25, 149.38, 143.23, 138.70, 115.63, 82.55, 47.93, 34.83, 16.87, 14.34. MS (ESI) 360 (M+H)$^+$.

EXAMPLE 98

5-Cyano-6-[5-(4-methanesulfonylphenyl)-oxazol-4-yl]-4-methyl-2-oxo-3,6-dihydro-2H-pyrimidine-1-carboxylic acid ethylamide Using 5-(4-methanesulfonylphenyl)oxazole-4-carboxaldehyde and following the procedure of Example 26, intermediate XXIV was obtained in 22% yield. The title compound was obtained in 63% yield following the procedure described in Example 28.

$^1$H-NMR (DMF-d$_7$, 400 MHz): δ 10.60 (s, 1H), 8.96 (t, J=4.8 Hz, 1H), 8.62 (s, 1H), 8.25 (d, J=8.3 Hz, 2H), 8.18 (d,

J=8.3 Hz, 2H), 6.67 (s, 1H), 3.37 (s, 3H), 3.25 (m, 2H), 2.21 (s, 3H), 1.07 (t, J=7.4 Hz, 3H). MS (ESI) 430 (M+H)+.

EXAMPLE 99

6-[5-(4-Chlorophenyl)-oxazol-4-yl]-5-cyano-4-methyl-2-oxo-3,6-dihydro-2H-pyrimidine-1-carboxylic acid ethylamide Using 5-(4-chlorophenyl)oxazol-4-carboxaldehyde and following the procedure of Example 26, intermediate XXIV was obtained in 40% yield. The title compound was obtained in 58% yield following the procedure described in Example 28.

$^1$H-NMR (DMSO-d$_6$, 400 MHz): δ 10.51 (s, 1H), 8.78 (m, 1H), 8.43 (s, 1H), 7.85 (d, 2H, J=8.5 Hz), 7.62 (d, 2H, J=8.5 Hz), 6.38 (s, 1H), 3.11 (m, 2H), 2.02 (s, 3H), 0.99 (t, 3H, J=7.2 Hz). $^{13}$C-NMR (DMSO-D$_6$, 400 MHz): δ 152.99, 152.51, 152.11, 149.30, 143.70, 134.17, 129.52, 128.13, 126.40, 117.20, 81.80, 48.09, 35.17, 17.28, 14.95. MS (ESI), 386 (M+H)+.

EXAMPLE 100

5-Cyano-4-methyl-2-oxo-6-[5-(4-trifluoromethylphenyl)-oxazol-4-yl]-3,6-dihydro-2H-pyrimidine-1-carboxylic acid ethylamide Using 5-(4-trifluoromethylphenyl)oxazole-4-carboxaldehyde and following the procedure of Example 26, intermediate XXIV was obtained in 31% yield. The title compound was obtained in 52% yield following the procedure described in Example 28.

$^1$H-NMR (DMSO-d$_6$, 400 MHz): δ 10.54 (s, 1H), 8.78 (m, 1H), 8.50 (s, 1H), 8.06 (d, 2H, J=8.1 Hz), 7.91 (d, 2H, J=8.1 Hz), 6.46 (s, 1H), 3.10 (m, 2H), 2.03 (s, 3H), 0.99 (t, 3H, J=7.2 Hz); $^{13}$C-NMR (DMSO-d$_6$, 400 MHz): δ 152.53, 152.31, 151.52, 149.03, 142.70, 134.96, 130.69, 126.41, 125.88, 116.62, 81.03, 47.69, 34.65, 16.75, 14.41; MS (ESI), 420.13 (M+H)+.

EXAMPLE 101

5-Cyano-4-methyl-2-oxo-6-(5-phenyloxazol-4-yl)-3,6-dihydro-2H-pyrimidine-1-carboxylic acid ethylamide Catalytic reduction (10% Pd/C, ammonium formate in refluxing acetonitrile) of the product of Example 99 gave the title compound in 45% yield.

$^1$H-NMR (CDCl$_3$, 400 MHz): δ 8.69 (m, 1H), 7.87 (m, 3H), 7.50 (m, 2H), 7.41 (m, 1H), 7.00 (s, 1H), 6.63 (s, 1H), 3.30 (m, 2H), 2.18 (s, 3H), 1.13 (t, 3H, J=7.2 Hz). $^{13}$CNMR (CDCl$_3$, 400 MHz): δ 152.40, 152.13, 150.25, 146.90, 132.60, 129.50, 129.12, 126.79, 116.57, 80.93, 48.25, 35.70, 17.87, 14.72; MS (ESI), 352.16 (M+H)+.

EXAMPLE 102

5-Cyano-4-methyl-[5-(4-nitrophenyl)-oxazol-4-yl]-2-oxo-3,6-dihydro-2H-pyrimidine-1-carboxylic acid ethylamide Using 5-(4-nitrophenyl)oxazole-4-carboxaldehyde and following the procedure of Example 26, intermediate XXIV was obtained in 36% yield. The title compound was obtained in 70% yield following the procedure described in Example 28.

$^1$H-NMR (DMSO-d$_6$, 400 MHz): δ 10.56 (s, 1H), 8.79 (m, 1H), 8.56 (s, 1H), 8.38 (m, 2H), 8.13 (m, 2H), 6.50 (s, 1H), 3.12 (m, 2H), 2.03 (s, 3H), 0.99 (t, 3H, J=7.2 Hz). $^{13}$C-NMR (DMSO-d$_6$, 400 MHz): δ 153.04, 152.37, 151.51, 149.13, 146.97, 136.16, 132.85, 126.72, 124.19, 116.57, 80.93, 47.87, 34.70, 16.81, 14.45. MS (ESI) 397 (M+H)+.

EXAMPLE 103

5-(4-Chlorophenyl)-2-(5-cyano-3-ethylcarbamoyl-6-methyl-2-oxo-1,2,3,4-tetrahydropyrimidin-4-yl)-furan-3-carboxylic acid ethyl ester Using 3-ethoxycarbonyl-5-(4-chlorophenyl)furan-2-carboxaldehyde and following the procedure of Example 26, intermediate XXIV was obtained in 59% yield. The title compound was obtained in 42% yield following the procedure described in Example 28.

$^1$H NMR (DMSO-d$_6$, 400 MHz): δ 1.02 (t, J=7.2 Hz, 3H), 1.34 (t, J=7.1 Hz, 3H), 2.07 (s, 3H), 3.16 (m, 2H), 4.30 (m, 2H), 6.85 (s, 1H), 7.34 (s, 1H), 7.53 (m, 2H), 7.65 (m, 2H), 8.67 (t, J=5.5 Hz, 1H), 10.76 (s, 1H). MS (ESI) 455 (M−H)−. HRMS (ESI) 455.1114 (M−H)−.

EXAMPLE 104

5-Cyano-4-methyl-2-oxo-6-(5-pyridin-3-yloxazol-4-yl)-3,6-dihydro-2H-pyrimidine-1-carboxylic acid ethylamide Using 5-(3-pyridinyl)oxazole-4-carboxaldehyde and following the procedure of Example 26, intermediate XXIV was obtained in 62% yield. The title compound was obtained in 41% yield following the procedure described in Example 28.

$^1$H-NMR (DMSO-d$_6$, 400 MHz): δ 10.53 (s, 1H), 9.04 (m, 1H), 8.77 (m, 1H), 8.67 (m, 1H), 8.50 (s, 1H), 8.22 (m, 1H), 7.60 (m, 1H), 6.40 (s, 2H), 3.12 (m, 2H), 2.04 (s, 3H), 1.00 (t, 3H, J=7.2 Hz). $^{13}$C-NMR (DMSO-d$_6$, 400 MHz): δ 152.76, 152.52, 151.75, 149.97, 149.19, 146.73, 134.73, 133.60, 124.06, 123.45, 116.94, 81.41, 47.81, 34.88, 16.99, 14.63; MS (ESI), 353.18 (M+H)+.

EXAMPLE 105

5-Cyano-4-methyl-2-oxo-6-(4-phenylthiazol-5-yl)-3,6-dihydro-2H-pyrimidine-1-carboxylic acid ethylamide Using 4-phenylthiazole-5-carboxaldehyde and following the procedure of Example 26, intermediate XXIV was obtained in 70% yield. The title compound was obtained in 27% yield following the procedure described in Example 28.

$^1$H-NMR (DMSO-d$_6$, 400 MHz): δ 10.70 (s, 1H), 9.08 (s, 1H), 8.71 (m, 1H), 7.73 (2H, m), 7.47 (m, 3H), 6.63 (s, 1H), 3.12 (m, 2H), 1.99 (s, 3H), 1.00 (t, 3H, J=7.2 Hz); $^{13}$C-NMR (DMSO-d$_6$, 400 MHz): δ 152.79, 151.97, 151.74, 150.61, 148.43, 133.87, 116.12, 83.68, 34.77, 16.69, 14.39. MS (ES) 368 (M+H)+.

EXAMPLE 106

[5-Cyano-4-methyl-6-(3-nitrophenyl)-2-oxo-3,6-dihydro-2H-pyrimidin-1-yl]-acetic acid tert-butyl ester Using 3-nitrobenzaldehyde and following the procedure of Example 26, intermediate XXIV was obtained in 92% yield and the title compound was obtained in 52% yield.

$^1$H-NMR (MeOH-d$_4$, 400 MHz): δ 8.28 (m, 1 H), 8.22 (t, 1 H, J=1.8 Hz), 7.76 (m, 1 H), 7.69 (t, 1 H, J=7.9 Hz), 7.62

(s, 1 H), 5.31 (s, 1 H), 4.23 (d, 1 H, J=17.6 Hz), 3.44 (d, 1 H, J=17.6 Hz), 2.16 (s, 3 H), 1.42 (s, 9 H). LC/MS (ES+) 395 (M+Na)+.

EXAMPLE 107

5-Cyano-4-methyl-6-(3-nitrophenyl)-2-oxo-3,6-dihydro-2H-pyrimidine-1-carboxylic acid isopropylamide Using 3-nitrobenzaldehyde and following the procedure of Example 26, intermediate XXIV was obtained in 92% yield. The title compound was obtained in 29% yield following the procedure described in Example 27.

$^1$H-NMR (MeOH-d$_4$, 400 MHz): δ 8.92 (s, 1 H), 8.22 (d, 1 H, J=8.3 Hz), 8.17 (t, 1 H, J=1.8 Hz), 7.74 (d, 1 H, J=6.6 Hz), 7.65 (m, 2 H), 6.31 (s, 1 H), 3.89 (m, 1 H), 2.19 (s, 3 H), 1.20 (d, 3 H, J=6.6 Hz), 1.16 (d, 3 H, J=6.6 Hz). LC/MS (ES+) 344 (M+H)+, 366 (M+Na)+.

EXAMPLE 108

5-Cyano-4-methyl-6-(3-nitrophenyl)-2-oxo-3,6-dihydro-2H-pyrimidine-1-carboxylic acid propylamide Using 3-nitrobenzaldehyde and following the procedure of Example 26, intermediate XXIV was obtained in 92% yield. The title compound was obtained in 22% yield following the procedure described in Example 27.

$^1$H-NMR (MeOH-d$_4$, 400 MHz) δ 9.09 (t, 1 H, J=5.3 Hz), 8.22 (m, 1 H), 8.17 (t, 1 H, J=1.8 Hz), 7.75 (d, 1 H, J=7.9 Hz), 7.65 (t, 1 H, J=7.9 Hz), 6.30 (s, 1 H), 3.33 (m, 2 H), 2.18 (s, 3 H), 1.54 (m, 2 H), 0.91 (t, 3 H, J=7.5 Hz). LC/MS (ES+) 344 (M+H)+, 366 (M+Na)+.

EXAMPLE 109

5-Cyano-4-methyl-6-(3-nitrophenyl)-2-oxo-3,6-dihydro-2H-pyrimidine-1-carboxylic acid phenylamide Using 3-nitrobenzaldehyde and following the procedure of Example 26, intermediate XXIV was obtained in 92% yield. The title compound was obtained in 10% yield following the procedure described in Example 27.

$^1$H-NMR (MeOH-d$_4$, 400 MHz): δ 11.18 (s, 1 H), 8.23 (m, 2 H), 7.81 (d, 1 H, J=7.9 Hz), 7.65 (m, 1 H), 7.44 (m, 2 H), 7.31 (t, 2 H, J=8.3 Hz), 7.11 (t, 1 H, J=8.3 Hz), 6.40 (s, 1 H), 2.23 (s, 3 H). LC/MS (ES+) 378 (M+H)+, 400 (M+Na)+.

EXAMPLE 110

5-Cyano-4-methyl-6-(3-nitrophenyl)-2-oxo-3,6-dihydro-2H-pyrimidine-1-carboxylic acid thiazol-2-ylamide Using 3-nitrobenzaldehyde and following the procedure of Example 26, intermediate XXIV was obtained in 92% yield. The title compound was obtained in 33% yield following the procedure described in Example 27.

$^1$H-NMR (MeOH-d$_4$, 400 MHz): δ 8.23 (m, 2 H), 7.80 (d, 1 H, J=7.5 Hz), 7.64 (t, 1 H, J=7.5 Hz), 7.42 (d, 1 H, J=4.0 Hz), 7.03 (d, 1 H, J=4.0 Hz), 6.36 (s, 1 H), 2.24 (d, 3 H, J=0.9 Hz). LC/MS (ES+) 385 (M+H)+, 407 (M+Na)+.

EXAMPLE 111

5-Cyano-4-methyl-6-(3-nitrophenyl)-2-oxo-3,6-dihydro-2H-pyrimidine-1-carboxylic acid (2,2,2-trifluoro-ethyl)-amide Using 3-nitrobenzaldehyde and following the procedure of Example 26, intermediate XXIV was obtained in 92% yield. The title compound was obtained in 25% yield following the procedure described in Example 27.

$^1$H-NMR (DMSO-d$_6$, 500 MHz): δ 10.77 (s, 1 H), 9.23 (t, 1 H, J=6.0 Hz), 8.21 (m, 1 H), 8.09 (s, 1 H), 7.75 (m, 2 H), 6.26 (s, 1 H), 4.01 (m, 2 H), 2.10 (s, 3 H).

EXAMPLE 112

5-Cyano-4-methyl-6-(3-nitrophenyl)-2-oxo-3,6-dihydro-2H-pyrimidine-1-carboxylic acid cyclopropylamide Using 3-nitrobenzaldehyde and following the procedure of Example 26, intermediate XXIV was obtained in 92% yield. The title compound was obtained in 19% yield following the procedure described in Example 27.

$^1$H-NMR (DMSO-d$_6$, 500 MHz): δ 10.62 (s, 1 H), 8.58 (s, 1 H), 8.21 (m, 1 H), 8.07 (d, 1 H, J=1.6 Hz), 7.73 (m, 2 H), 6.22 (s, 1 H), 2.62 (m, 1 H), 2.09 (s, 3 H), 0.64 (m, 2 H), 0.46 (m, 2 H).

EXAMPLE 113

5-Cyano-4-methyl-6-(3-nitrophenyl)-2-oxo-3,6-dihydro-2H-pyrimidine-1-carboxylic acid (2-hydroxyethyl)-amide Using 3-nitrobenzaldehyde and following the procedure of Example 26, intermediate XXIV was obtained in 92% yield. The tide compound was obtained in 23% yield following the procedure described in Example 27.

$^1$H-NMR (CDCl$_3$, 500 MHz): δ 8.93 (s, 1 H), 8.15 (d, 1 H, J=7.9 Hz), 8.07 (s, 1 H), 7.68 (d, 1 H, J=7.9 Hz), 7.51 (t, 1 H, J=7.9 Hz), 6.86 (s, 1 H), 6.30 (s, 1 H), 3.67 (m, 2 H), 3.43 (m, 1 H), 3.36 (m, 1 H), 2.18 (s, 3 H). LC/MS (ES+) 346 (M+H)+.

EXAMPLE 114

3-(4,5-Dihydrooxazol-2-yl)-6-methyl-6-(3-nitrophenyl)-2-oxo-1,2,3,4-tetrahydropyrimidine-5-carbonitrile Prepared from the product of Example 113 (Burgess reagent in refluxing tetrahydrofuran) in 71% yield.

$^1$H-NMR (MeOH-d$_4$, 400 MHz): δ 8.10 (m, 2 H), 7.66 (d, 1 H, J=7.9 Hz), 7.56 (t, 1 H, J=7.9 Hz), 6.19 (s, 1 H), 4.04 (m, 2 H), 3.50 (m, 1 H), 3.39 (m, 1 H), 2.06 (s, 3 H). LC/MS (ES+) 328 (M+H)+.

EXAMPLE 115

5-Cyano-4-methyl-6-(3-nitrophenyl)-2-oxo-3,6-dihydro-2H-pyrimidine-1-carboxylic acid allylamide Using 3-nitrobenzaldehyde and following the procedure of Example 26, intermediate XXIV was obtained in 92% yield. The title compound was obtained in 36% yield following the procedure described in Example 27.

$^1$H-NMR (DMSO-d$_6$, 500 MHz): δ 10.65 (s, 1 H), 8.92 (t, 1 H, J=5.5 Hz), 8.21 (m, 1 H), 8.08 (s, 1 H), 7.74 (m, 2 H), 6.24 (s, 1 H), 5.81 (m, 1 H), 5.07 (m, 2 H), 3.78 (m, 2 H), 2.10 (s, 3 H). LC/MS (ES+) 342 (M+H)+, 364 (M+Na)+.

What is claimed is:
1. A compound of formula I

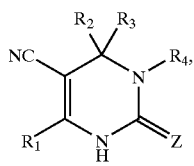

its enantiomers, diastereomers, or pharmaceutically acceptable salts, and solvates thereof, wherein
$R_1$ is selected from the group consisting of hydrogen, alkyl and cycloalkyl;
$R_2$ is aryl, or heteroaryl;
$R_3$ is H;
$R_4$ is selected from the group consisting of alkyl, arylalkyl, cycloalkylalkyl, heteroarylalkyl, heterocycloalkyl, aminoalkyl, heterocycloalkylalkyl, CN, C(O)$R_5$, CO$_2R_5$, C(O)S$R_5$ and CONR$_5R_6$;
$R_5$ and $R_6$ are each independently selected from the group consisting of H, alkyl, cycloalkyl, hydroxyalkyl, alkenyl, alkoxy, thioalkoxy, alkoxyalkyl, haloalkyl, aryl, heteroaryl, arylalkyl, cycloalkylalkyl, heteroarylalkyl and heterocycloalkylalkyl or N—$R_5R_6$ together form a heterocycloalkyl
Z is selected from the group consisting of O, S and NR$_6$;
$R_8$ is selected from the group consisting of H, CN, sulfonamido, OR$_7$, alkyl, cycloalkyl, aryl, arylalkyl, heterocyclyl, heteroaryl and heteroarylalkyl; and
$R_7$ is selected from the group consisting of H, alkyl, arylalkyl, cycloalkylalkyl, heterocycloalkylalkyl and heteroarylalkyl.
2. The compound of claim 1 wherein $R_2$ is heteroaryl.
3. The compound of claim 2 wherein $R_2$ is an optionally substituted thiophene, oxazole, isoxazole, or furan.
4. The compound of claim 2 wherein said heteroaryl is substituted with methyl, ethyl, halo, haloalkyl, or aryl.
5. The compound of claim 1 wherein $R_2$ is a substituted phenyl.
6. The compound of claim 5 wherein said phenyl is substituted with alkyl, alkoxy, alkoxyalkyl, cyano, halo, haloalkyl, nitro, amino CO$_2R_5$, CONR$_5R_6$, alkenyloxy, aryloxy, wherein $R_5$ and $R_6$ are, independently, H or alkyl.
7. The compound of claim 6 wherein said phenyl is substituted with methyl, methoxy, F, Cl, CF$_3$, dimethylamimo, or ethoxymethyl.
8. The compound of claim 1 wherein $R_1$ is alkyl; $R_4$ is selected from the group consisting of alkyl, arylalkyl, CO$_2R_5$, and CONR$_5R_6$; $R_5$ and $R_6$ are independently selected from the group consisting of H, alkyl, aminoalkyl, hydroxyalkyl, phenylamino and arylalkyl; Z is selected from the group consisting of O, S, and NR$_8$; $R_8$ is selected from the group consisting of H and CN.
9. The compound of claim 1 wherein $R_4$ is selected from the group consisting of alkyl, arylalkyl, C(O)$R_5$ CO$_2R_5$, C(O)S$R_5$ and CONR$_5R_6$.
10. The compound of claim 1 wherein $R_4$ is CO$_2R_5$; Z is O; and $R_5$ is ethyl.
11. The compound of claim 1 wherein $R_4$ is CONR$_5R_6$; Z is O; $R_5$ is H and $R_6$ is methyl, ethyl, propyl, phenyl, cyclopropyl, hydroxyethyl, thiophene, or 2-propylene.
12. The compound of claim 1 wherein $R_4$ is selected from the group consisting of alkyl and arylalkyl, and Z is O.
13. The compound of claim 1 wherein $R_1$ is CH$_3$; $R_2$ is aryl; $R_4$ is CO$_2R_5$; $R_5$ is alkyl; and Z is O.
14. The compound of claim 1 wherein $R_1$ is CH$_3$; $R_2$ is aryl; $R_4$ is CONR$_5R_6$; $R_5$ is alkyl; $R_6$ is H and Z is O.
15. The compound of claim 1 wherein $R_1$ is CH$_3$; $R_2$ is heteroaryl; $R_4$ is CO$_2R_5$ or CONR$_5R_6$; $R_6$ is H and $R_5$ is ethyl.
16. The compound of claim 1 selected from the group consisting of:
5-cyano-3,6-dihydro-4-methyl-6-(3-nitrophenyl)-2-thioxo-1-(2H)-pyrimidinecarboxylic acid, 1-ethyl ester;
5-cyano-3,6-dihydro-4-methyl-6-(3-nitrophenyl)-2-oxo-1-(2H)-pyrimidinecarboxylic acid, 1-ethyl ester;
5-cyano-3,6-dihydro-4-methyl-6-(3-nitrophenyl)-2-oxo-1-(2H)-pyrimidinecarboxylic acid, 1-ethyl amide;
5-cyano-3,6-dihydro-4-methyl-6-(3-nitrophenyl)-2-oxo-1-(1-oxobutyl)-(2H)-pyrimidine;
5-cyano-3,6-dihydro-4-methyl-6-(3-aminophenyl)-2-oxo-1-(2H)-pyrimidinecarboxylic acid, 1-ethyl ester;
5-cyano-3,6-dihydro-4-methyl-6-(3-aminophenyl)-2-oxo-1-(2H)-pyrimidinecarboxylic acid, 1-ethyl ester;
5-cyano-3,6-dihydro-4-methyl-6-(3-(N,N-dimethyl)aminophenyl)-2-oxo-1-(2H)-pyrimidinecarboxylic acid, 1-ethyl ester;
5-cyano-3,6-dihydro-4-methyl-6-(3-trifluoromethylphenyl)-2-oxo-1-(2H)-pyrimidinecarboxylic acid, 1-ethyl ester;
5-cyano-3,6-dihydro-4-methyl-6-(2,3-dichlorophenyl)-2-oxo-1-(2H)-pyrimidinecarboxylic acid, 1-ethyl ester;
5-cyano-3,6-dihydro-4-methyl-6-(3-methoxyphenyl)-2-oxo-1-(2H)-pyrimidinecarboxylic acid, 1-ethyl ester;
5-cyano-3,6-dihydro-4-methyl-6-(3,5-dichlorophenyl)-2-oxo-1-(2H)-pyrimidinecarboxylic acid, 1-ethyl ester;
5-cyano-3,6-dihydro-4-methyl-6-(3,4-dichlorophenyl)-2-oxo-1-(2H)-pyrimidinecarboxylic acid, 1-ethyl ester;
5-cyano-3,6-dihydro-4-methyl-6-(3-cyanophenyl)-2-oxo-1-(2H)-pyrimidinecarboxylic acid, 1-ethyl ester;
5-cyano-3,6-dihydro-4-methyl-6-(4-methoxyphenyl)-2-oxo-1-(2H)-pyrimidinecarboxylic acid, 1-ethyl ester;
5-cyano-3,6-dihydro-4-methyl-6-(4-methylphenyl)-2-oxo-1-(2H)-pyrimidinecarboxylic acid, 1-ethyl ester;
5-cyano-3,6-dihydro-4-methyl-6-phenyl-2-oxo-1-(2H)-pyrimidinecarboxylic acid, 1-ethyl ester;
5-cyano-3,6-dihydro-4-methyl-6-(2-methylphenyl)-2-oxo-1-(2H)-pyrimidinecarboxylic acid, 1-ethyl ester.
17. A compound selected from the group consisting of:
5-cyano-3,6-dihydro-4-methyl-6-(3-chlorophenyl)-2-oxo-1-(2H)-pyrimidinecarboxylic acid, 1-ethyl ester;
5-cyano-3,6-dihydro-4-methyl-6-(3-fluorophenyl)-2-oxo-1-(2H)-pyrimidinecarboxylic acid, 1-ethyl ester;
5-cyano-3,6-dihydro-4-methyl-6-(4-chlorophenyl)-2-oxo-1-(2H)-pyrimidinecarboxylic acid, 1-ethyl ester;
5-cyano-3,6-dihydro-4-methyl-6-(4-fluorophenyl)-2-oxo-1-(2H)-pyrimidinecarboxylic acid, 1-ethyl ester; and
5-cyano-3,6-dihydro-4-methyl-6-(2-fluorophenyl)-2-oxo-1-(2H)-pyrimidinecarboxylic acid, 1-ethyl ester;
6-(3,5-Bis-trifluoromethylphenyl)-5-cyano-4-methyl-2-oxo-3,6-dihydro-2H-pyrimidine-1-carboxylic acid ethyl ester;
5-Cyano-4-methyl-6-(3-nitrophenyl)-2-oxo-3,6-dihydro-2H-pyrimidine-1-carboxylic acid methylamide;
5-Cyano-4-methyl-2-oxo-6-phenyl-3,6-dihydro-2H-pyrimidine-1-carboxylic acid ethylamide;

5-Cyano-6-(3,5-dichlorophenyl)-4-methyl-2-oxo-3,6-dihydro-2H-pyrimidine-1-carboxylic acid 2-methoxyethyl ester;

5-Cyano-4-methyl-2-oxo-6-(3-trifluoromethylphenyl)-3,6-dihydro-2H-pyrimidine-1-carboxylic acid ethylamide;

5-Cyano-6-(3,5-dichlorophenyl)-4-methyl-2-oxo-3,6-dihydro-2H-pyrimidine-1-carboxylic acid ethylamide;

3-Butyryl-4-(3,5-dichlorophenyl)-6-methyl-2-oxo-1,2,3,4-tetrahydropyrimidine-5-carbonitrile;

5-Cyano-4-methyl-2-oxo-6-(3-trifluoromethylphenyl)-3,6-dihydro-2H-pyrimidine-1-carboxylic acid (2-dimethylamino-ethyl)-amide;

5-Cyano-4-methyl-2-oxo-6-(3-trifluoromethylphenyl)-3,6-dihydro-2H-pyrimidine-1-carbothioic acid S-ethyl ester;

5-cyano-4-methyl-2-oxo-6-(3-trifluoromethylphenyl)-3,6-dihydro-2H-pyrimidine-1-carboxylic acid (2-hydroxy-ethyl)-amide;

4-(3,5-Dichlorophenyl)-6-methyl-2-oxo-3-(thiophene-2-carbonyl)-1,2,3,4-tetrahydropyrimidine-5-carbonitrile;

5-Cyano-6-(3,5-difluorophenyl)-4-methyl-2-oxo-3,6-dihydro-2H-pyrimidine-1-carboxylic acid ethylamide;

5-Cyano-6-(3,5-difluorophenyl)-4-methyl-2-oxo-3,6-dihydro-2H-pyrimidine-1-carboxylic acid ethyl ester.

18. A compound selected from the following:

4-(3,5-Difluorophenyl)-6-methyl-2-oxo-3-(piperidine-1-carbonyl)-1,2,3,4-tetrahydropyrimidine-5-carbonitrile;

4-(3,5-Difluorophenyl)-6-methyl-2-oxo-3-pyrrolidine-1-carbonyl)-1,2,3,4-trahydropyrimidine-5-carbonitrile 5-Cyano-4-methyl-6-naphthalen-1-yl-2-oxo-3,6-dihydro-2H-pyrimidine-1-carboxylic acid ethyl ester;

5-Cyano-4-methyl-6-naphthalen-1-yl-2-oxo-3,6-dihydro-2H-pyrimidine-1-carboxylic acid ethylamide;

6-(3-Bromophenyl)-5-cyano-4-methyl-2-oxo-3,6-dihydro-2H-pyrimidine-1-carboxylic acid ethyl ester;

6-(3-Bromophenyl)-5-cyano-4-methyl-2-oxo-3,6-dihydro-2H-pyrimidine-1-carboxylic acid ethylamide;

5-Cyano-4-methyl-2-oxo-6-(2-trifluoromethylphenyl)-3,6-dihydro-2H-pyrimidine-1-carboxylic acid ethyl ester; 5-Cyano-4-methyl-2-oxo-6-(2-trifluoromethylphenyl)-3,6-dihydro-2H-pyrimidine-1-carboxylic acid ethylamide; 5-Cyano-6-(3-methoxycarbonylphenyl)-4-methyl-2-oxo-3,6-dihydro-2H-pyrimidine-1-carboxylic acid ethyl ester;

3-(5-Cyano-3-ethylcarbamoyl-6-methyl-2-oxo-1,2,3,4-tetrahydropyrimidin-4-yl)-benzoic acid methyl ester;

6-(3,5-Bis-trifluoromethylphenyl-5-cyano-4-methyl-2-oxo-3,6-dihydro-2H-pyrimidine-1-carboxylic acid ethylamide;

6-(2,5-Bis-trifluoromethylphenyl)-5-cyano-4-methyl-2-oxo-3,6-dihydro-2H-pyrimidine-1-carboxylic acid ethylamide;

6-(2,5-Bis-trifluoromethylphenyl)-5-cyano-4-methyl-2-oxo-3,6-dihydro-2H-pyrimidine-1-carboxylic acid ethyl ester;

5-Cyano-6-(3-ethylcarbamoylphenyl)-4-methyl-2-oxo-3,6-dihydro-2H-pyrimidine-1-carboxylic acid ethylamide;

5-Cyano-6-(3-cyano-4-fluorophenyl)-4-methyl-2-oxo-3,6-dihydro-2H-pyrimidine-1-carboxylic acid ethylamide;

5-Cyano-6-(3-cyano-4-fluorophenyl)-4-methyl-2-oxo-3,6-dihydro-2H-pyrimidine-1-carboxylic acid ethyl ester;

5-Cyano-6-(2-fluoro-5-trifluoromethylphenyl)-4-methyl-2-oxo-3,6-dihydro-2H-pyrimidine-1-carboxylic acid ethylamide.

19. A compound selected from the group consisting of:

5-Cyano-6-(2-fluoro-5-trifluoromethylphenyl)-4-methyl-2-oxo-3,6-dihydro-2H-pyrimidine-1-carboxylic acid ethyl ester;

5-Cyano-4-methyl-6-naphthalen-2-yl-2-oxo-3,6-dihydro-2H-pyrimidine-1-carboxylic acid ethyl ester;

5-Cyano-6-[3-(2-hydroxyethylcarbamoyl)-phenyl]-4-methyl-2-oxo-3,6-dihydro-2H-pyrimidine-1-carboxylic acid ethylamide;

5-Cyano-6-(2-methoxyphenyl)-4-methyl-2-oxo-3,6-dihydro-2H-pyrimidine-1-carboxylic acid ethyl ester;

5-Cyano-6-(2-methoxyphenyl)-4-methyl-2-oxo-3,6-dihydro-2H-pyrimidine-1-carboxylic acid ethylamide;

6-(2-Allyloxyphenyl)-5-cyano-4-methyl-2-oxo-3,6-dihydro-2H-pyrimidine-1-carboxylic acid ethyl ester;

6-(2-Allyloxyphenyl)-5-cyano-4-methyl-2-oxo-3,6-dihydro-2H-pyrimidine-1-carboxylic acid ethylamide;

6-(2-Bromophenyl)-5-cyano-4-methyl-2-oxo-3,6-dihydro-2H-pyrimidine-1-carboxylic acid ethyl ester;

6-(2-Bromophenyl)-5-cyano-4-methyl-2-oxo-3,6-dihydro-2H-pyrimidine-1-carboxylic acid ethylamide 5-Cyano-6-(3-methoxyphenyl)-4-methyl-2-oxo-3,6-dihydro-2H-pyrimidine-1-carboxylic acid ethylamide;

6-(2-Benzyloxyphenyl)-5-cyano-4-methyl-2-oxo-3,6-dihydro-2H-pyrimidine-1-carboxylic acid ethyl ester;

6-(3-Bromo-4-fluorophenyl)-5-cyano-4-methyl-2-oxo-3,6-dihydro-2H-pyrimidine-1-carboxylic acid ethylamide;

6-(3-Bromo-4-fluorophenyl)-5-cyano-4-methyl-2-oxo-3,6-dihydro-2H-pyrimidine-1-carboxylic acid cyclopropylamide; and 6-(5-Bromo-2-fluorophenyl)-5-cyano-4-methyl-2-oxo-3,6-dihydro-2H-pyrimidine-1-carboxylic acid ethylamide.

20. A compound selected from the group consisting of:

6-(5-Bromo-2-fluorophenyl)-5-cyano-4-methyl-2-oxo-3,6-dihydro-2H-pyrimidine-1-carboxylic acid cyclopropylamide;

5-Cyano-6-(3,5-dibromophenyl)-4-methyl-2-oxo-3,6-dihydro-2H-pyrimidine-1-carboxylic acid ethylamide;

5-Cyano-4-methyl-6-(3-nitrophenyl)-2-oxo-3,6-dihydro-2H-pyrimidine-1-carboxylic acid cyclopropylmethylamide;

5-Cyano-4-methyl-2-oxo-6-thiophen-3-yl-3,6-dihydro-2H-pyrimidine-1-carboxylic acid ethyl ester;

5-Cyano-4-methyl-6-(5-methylisoxazol-3-yl)-2-oxo-3,6-dihydro-2H-pyrimidine-1-carboxylic acid ethyl ester;

5-Cyano-6-(3,5-dimethylisoxazol-4-yl)-4-methyl-2-oxo-3,6-dihydro-2H-pyrimidine-1-carboxylic acid ethyl ester;

5-Cyano-4-methyl-2-oxo-6-thiophen-2-yl-3,6-dihydro-2H-pyrimidine-1-carboxylic acid ethyl ester;

5-Cyano-4-methyl-6-(3-methylthiophen-2-yl)-2-oxo-3,6-dihydro-2H-pyrimidine-1-carboxylic acid ethylamide;

5-Cyano-4-methyl-6-(3-methylthiophen-2-yl)-2-oxo-3,6-dihydro-2H-pyrimidine-1-carboxylic acid ethyl ester;

5-Cyano-4-methyl-6-(2-methylthiazol-4-yl)-2-oxo-3,6-dihydro-2H-pyrimidine-1-carboxylic acid ethyl ester;

6-(4-Bromothiophen-2-yl)-5-cyano-4-methyl-2-oxo-3,6-dihydro-2H-pyrimidine-1-carboxylic acid ethylamide;

6-(4-Bromothiophen-2-yl)-5-cyano-4-methyl-2-oxo-3,6-dihydro-2H-pyrimidine-1-carboxylic acid ethyl ester;

5-Cyano-4-methyl-2-oxo-6-[2-(4-trifluoromethylphenyl)-thiazol-4-yl]-3,6-dihydro-2H-pyrimidine-1-carboxylic acid ethyl ester;

6-[5-(4-Chlorophenyl)-oxazol-4-yl]-5-cyano-4-methyl-2-oxo-3,6-dihydro-2H-pyrimidine-1-carboxylic acid ethyl ester; and 6-(2-Bromothiazol-5-yl)-5-cyano-4-methyl-2-oxo-3,6-dihydro-2H-pyrimidine-1-carboxylic acid ethyl ester.

21. A compound selected from the group consisting of:

6-(5-Bromo-2-fluorophenyl)-5-cyano-4-methyl-2-oxo-3,6-dihydro-2H-pyrimidine-1-carboxylic acid cyclopropylamide;

5-Cyano-6-(3,5-dibromophenyl)-4-methyl-2-oxo-3,6-dihydro-2H-pyrimidine-1-carboxylic acid ethylamide;

5-Cyano-4-methyl-6-(3-nitrophenyl)-2-oxo-3,6-dihydro-2H-pyrimidine-1-carboxylic acid cyclopropylmethylamide;

5-Cyano-4-methyl-2-oxo-6-phenethyloxymethyl-3,6-dihydro-2H-pyrimidine-1-carboxylic acid ethyl ester;

5-Cyano-4-methyl-2-oxo-6-phenethyl-3,6-dihydro-2H-pyrimidine-1-carboxylic acid ethylamide;

5-Cyano-4-methyl-2-oxo-6-thiophen-3-yl-3,6-dihydro-2H-pyrimidine-1-carboxylic acid ethyl ester;

5-Cyano-4-methyl-6-(-5-methylisoxazol-3-yl)-2-oxo-3,6-dihydro-2H-pyrimidine-1-carboxylic acid ethyl ester;

5-Cyano-6-(3,5-dimethylisoxazol-4-yl)-4-methyl-2-oxo-3,6-dihydro-2H-pyrimidine-1-carboxylic acid ethyl ester;

5-Cyano-4-methyl-2-oxo-6-thiophen-2-yl-3,6-dihydro-2H-pyrimidine-1-carboxylic acid ethyl ester;

5-Cyano-4-methyl-6-(3-methylthiophen-2-yl)-2-oxo-3,6-dihydro-2H-pyrimidine-1-carboxylic acid ethylamide;

5-Cyano-4-methyl-6-(3-methylthiophen-2-yl)-2-oxo-3,6-dihydro-2H-pyrimidine-1-carboxylic acid ethyl ester;

5-Cyano-4-methyl-6-(2-methylthiazol-4-yl)-2-oxo-3,6-dihydro-2H-pyrimidine-1-carboxylic acid ethyl ester;

6-(4-Bromothiophen-2-yl)-5-cyano-4-methyl-2-oxo-3,6-dihydro-2H-pyrimidine-1-carboxylic acid ethylamide;

6-(4-Bromothiophen-2-yl)-5-cyano-4-methyl-2-oxo-3,6-dihydro-2H-pyrimidine-1-carboxylic acid ethyl ester;

5-Cyano-4-methyl-2,-oxo-6-[2-(4-trifluoromethylphenyl)-thiazol-4-yl]-3,6-dihydro-2H-pyrimidine-1-carboxylic acid ethyl ester;

6-[5-(4-Chlorophenyl)-oxazol-4-yl]-5-cyano-4-methyl-2-oxo-3,6-dihydro-2H-pyrimidine-1-carboxylic acid ethyl ester; and 6-(2-Bromothiazol-5-yl)-5-cyano-4-methyl-2-oxo-3,6-dihydro-2H-pyrimidine-1-carboxylic acid ethyl ester.

22. A compound selected from the group consisting of:

5-Cyano-4-methyl-2-oxo-6-(4-phenylthiophen-2-yl)-3,6-dihydro-2H-pyrimidine-1-carboxylic acid ethylamide;

6-[5-(4-Chlorophenyl)-furan-2-yl]-5-cyano-4-methyl-2-oxo-3,6-dihydro-2H-pyrimidine-1-carboxylic acid ethylamide;

5-Cyano-4-methyl-2-oxo-6-(4-trifluoromethylthiazol-5-yl)-3,6-dihydro-2H-pyrimidine-1-carboxylic acid ethyl ester;

5-Cyano-4-methyl-2-oxo-6-(4-trifluoromethylthiazol-5-yl)-3,6-dihydro-2H-pyrimidine-1-carboxylic acid ethylamide;

5-Cyano-6-[5-(4-methanesulfonylphenyl)-oxazol-4-yl]-4-methyl-2-oxo-3,6-dihydro-2H-pyrimidine-1-carboxylic acid ethylamide;

6-[5-(4-Chlorophenyl)-oxazol-4-yl]-5-cyano-4-methyl-2-oxo-3,6-dihydro-2H-pyrimidine-1-carboxylic acid ethylamide;

5-Cyano-4-methyl-2-oxo-6-[5-(4-trifluoromethylphenyl)-oxazol-4-yl]-3,6-dihydro-2H-pyrimidine-1-carboxylic acid ethylamide;

5-Cyano-4-methyl-2-oxo-6-(5-phenyloxazol-4-yl)-3,6-dihydro-2H-pyrimidine-1-carboxylic acid ethylamide;

5-Cyano-4-methyl-6-[5-(4-nitrophenyl)-oxazol-4-yl]-2-oxo-3,6-dihydro-2H-pyrimidine-1-carboxylic acid ethylamide;

5-(4-Chlorophenyl)-2-(5-cyano-3-ethylcarbamoyl-6-methyl-2-oxo-1,2,3,4-tetrahydropyrimidin-4-yl)-furan-3-carboxylic acid ethyl ester;

5-Cyano-4-methyl-2-oxo-6-(5-pyridin-3-yloxazol-4-yl)-3,6-dihydro-2H-pyrimidine-1-carboxylic acid ethylamide;

5-Cyano-4-methyl-2-oxo-6-(4-phenylthiazol-5-yl)-3,6-dihydro-2H-pyrimidine-1-carboxylic acid ethylamide;

[5-Cyano-4-methyl-6-(3-nitrophenyl)-2-oxo-3,6-dihydro-2H-pyrimidin-1-yl]-acetic acid tert-butyl ester;

5-Cyano-4-methyl-6-(3-nitrophenyl)-2-oxo-3,6-dihydro-2H-pyrimidine-1-carboxylic acid isopropylamide;

5-Cyano-4-methyl-6-(3-nitrophenyl)-2-oxo-3,6-dihydro-2H-pyrimidine-1-carboxylic acid propylamide;

5-Cyano-4-methyl-6-(3-nitrophenyl)-2-oxo-3,6-dihydro-2H-pyrimidine-1-carboxylic acid phenylamide; and 5-Cyano-4-methyl-6-(3-nitrophenyl)-2-oxo-3,6-dihydro-2H-pyrimidine-1-carboxylic acid thiazol-2-ylamide.

23. A compound selected from the group consisting of:

5-Cyano-4-methyl-6-(3-nitrophenyl)-2-oxo-3,6-dihydro-2H-pyrimidine-1-carboxylic acid (2,2,2-trifluoroethyl)-amide;

5-Cyano-4-methyl-6-(3-nitrophenyl)-2-oxo-3,6-dihydro-2H-pyrimidine-1-carboxylic acid cyclopropylamide;

5-Cyano-4-methyl-6-(3-nitrophenyl)-2-oxo-3,6-dihydro-2H-pyrimidine-1-carboxylic acid (2-hydroxy-ethyl)-amide;

3-(4,5-Dihydrooxazol-2-yl)-6-methyl-4-(3-nitrophenyl)-2-oxo-1,2,3,4-tetrahydropyrimidine-5-carbonitrile; and 5-Cyano-4-methyl-6-(3-nitrophenyl)-2-oxo-3,6-dihydro-2H-pyrimidine-1-carboxylic acid allylamide.

24. A method of preparing a compound having the following formula:

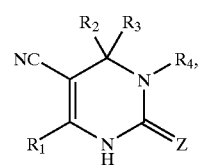

I wherein $R_1$ is selected from the group consisting of hydrogen, alkyl and cycloalkyl;

$R_2$ is aryl or heteroaryl;

$R_3$ is H;

$R_4$ is selected from the group consisting of alkyl, arylalkyl, cycloalkylalkyl, heteroarylalkyl, heterocycloalkyl, aminoalkyl, heterocycloalkylalkyl, CN, C(O)R$_5$, CO$_2$R$_5$, C(O)SR$_5$ and CONR$_5$R$_6$;

R$_5$ and R$_6$ are each independently selected from the group consisting of H, alkyl, cycloalkyl, hydroxyalkyl, alkenyl, alkoxy, thioalkoxy, alkoxyalkyl, haloalkyl, aryl, heteroaryl, arylalkyl, cycloalkylalkyl, heteroarylalkyl and heterocycloalkylalkyl or N-R$_5$R$_6$ together form a heterocycloalkyl Z is selected from the group consisting of O, S and NR$_8$;

R$_8$ is selected from the group consisting of H, CN, sulfonamido, OR$_7$, alkyl, cycloalkyl, aryl, arylalkyl, heterocyclyl, heteroaryl and heteroarylalkyl; and R$_7$ is selected from the group consisting of H, alkyl, arylalkyl, cycloalkylalkyl, heterocycloalkylalkyl and heteroarylalkyl;

comprising the steps of contacting a compound having formula R$_2$COR$_3$ with a compound having the formula R$_1$COCH$_2$CN or a compound having the formula

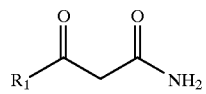

in the presence of polyphosphate ester and urea to form

XXIV

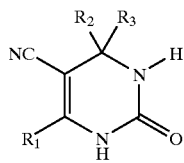

further comprising contacting compound XXIV with R$_4$—X, wherein X is a leaving group, in the presence of a base to yield a compound having formula I

I

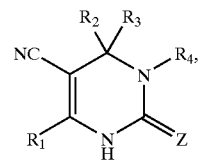

25. A pharmaceutical composition comprising a compound of claim 1 and a pharmaceutically acceptable carrier.

26. The pharmaceutical composition of claim 25 further comprising at least one other anti-cancer agent formulated as a fixed dose.

27. A method for treating a proliferative disease via modulation of the Eg5 motor protein comprising administering to a mammalian species in need of such treatment an effective amount of at least one compound of claim 1.

28. The method according to claim 27 further comprising administering to said mammalian species at least one other anti-cancer agent.

29. The method according to claim 27 wherein the proliferative disease is cancer.

30. A method for treating a proliferative disease by inducing apoptosis comprising administering to a mammalian species an effective amount of a compound of claim 1.

31. The method according to claim 30 further comprising administering to said mammalian species at least one other anti-cancer agent.

32. The method according to claim 30 wherein the proliferative disease is cancer.

* * * * *